(12) United States Patent
Luo

(10) Patent No.: US 6,864,359 B1
(45) Date of Patent: *Mar. 8, 2005

(54) STRUCTURE-BASED SCREENING TECHNIQUES FOR DRUG DISCOVERY

(75) Inventor: Peizhi Luo, Arcadia, CA (US)

(73) Assignee: Xencor, Monrovia, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 94 days.

(21) Appl. No.: 09/502,984

(22) Filed: Feb. 11, 2000

Related U.S. Application Data

(60) Provisional application No. 60/120,009, filed on Feb. 11, 1999, and provisional application No. 60/131,674, filed on Apr. 29, 1999.

(51) Int. Cl.[7] .................. A61K 35/14; A61K 38/16; C07K 1/00

(52) U.S. Cl. .................. 530/380; 530/350

(58) Field of Search ............... 435/6, 7.1, 7.8, 435/7.92, 69.1, 69.7, 70.1, 91.1, 455, 335, 468, 336, 471, 440; 530/300, 350, 380, 829; 436/501, 518, 519, 524; 536/23.1, 23.5

(56) References Cited

U.S. PATENT DOCUMENTS

| | | | |
|---|---|---|---|
| 5,292,654 A | | 3/1994 | Yoshimura et al. |
| 5,844,099 A | * | 12/1998 | Stahl et al. .................. 530/350 |
| 5,889,143 A | * | 3/1999 | Ochoa et al. ............... 530/300 |
| 5,968,752 A | * | 10/1999 | Ichijo et al. ................. 435/7.2 |
| 6,093,547 A | * | 7/2000 | Jin et al. ..................... 435/7.1 |

FOREIGN PATENT DOCUMENTS

| | | |
|---|---|---|
| EP | 0 603 8787 | 2/1994 |
| EP | 0 742 438 | 11/1996 |
| WO | 94/29458 | 12/1994 |
| WO | 98/47089 | 10/1998 |

OTHER PUBLICATIONS

Dahiyat et al., "Protein design automation," *Protein Science*, 5:895–903 (1996).

Jolliffe et al., "Erythropoietin Receptor: Application in Drug Development," Nephrol. Cial. Transplant., 10(suppl. 2): 28–34 (1995).

Quelle et al., "Mutations in the WSAWSE and Cytosolic Domains of the Erythropoietin Receptor Affect Signal Transduction and Ligand Binding and Internalization," Molecular and Cellular Biology, 12(10): 4553–4561 (1992).

Barbone et al., "Mutagenesis Studies of the Human Erthropoietin Receptor," The Journal of Biological Chemistry, 272(8): 4985–4992 (1997).

Johnson et al., "Refolding, Purification, and Characterization of Human Erythropoietin Binding Protein Produced in *Escherichia coli*," Protein Expression and Purification, 7:104–113 (1996).

Livnah et al., "An Antagoisnt Peptide–EPO Receptor Complex Suggests that Receptor Dimerization is not Sufficient for Actviation," Nature Structural Biology, 5(11): 993–1003 (1998).

McConnell et al., Isolation of Erythropoietin Recetpor Agonist Peptides Using Evolved Phage Libraries, Biol. Chem., 379:1279–1286 (1998).

Wrighton et al., "Small Peptides as potent Mimetics of the Protein Hormone Erythropoietin," Science, 273:458–463 (1996).

Edgington, S. "Superfamily Structure And Biotech Drug Development," Biotechnology, 10:1529–1534 (1992).

Middleton et al., "Critical Erythropoietin (EPO) Binding Determinanats on the EPO Receptor also Interact," Blood, 88(10): 661A, abstract (1996).

Borman, "Proteins to Order," Chemical and Engineering Newsletter (C&EN) Oct. 6, 1997, 9–10 (1997).

Lazar et al., "De novo design of the hydrophobic core of ubiquitin," Protein Science 6:1167–1178 (1997).

Desjarlais et al., "New strategies in protein design," Current Opinion in Biotechnology 6:460–466 (1995).

Wodak, S.J., et al., "Analytical approximation to the accessible surface area of proteins", *Proc. Natl. Acad. Sci. USA* vol. 77(4):1736–1740 (Apr. 1980).

Muñoz, V., et al., "Analysis of the effect of local interactions on protein stability", *Folding & Design* 1(3):167–178 (Apr. 1996).

Dunbrack Jr., R.L., et al., "Conformational analysis of the backbone–dependent rotamer preferences of protein sidechains", *Struc. Biol.* vol. 1(5):334–340 (May 1994).

Hellinga, H.W., et al., "Construction of New Ligand Binding Site in Proteins of Known Structure", *J. Mol. Biol.* 222:763–785 (1991).

Desmet, J., et al., "The Dead End Elimination' Theorem as a New Approach to the Side Chain Packing Protein", from "The Protein Folding Problem and Tertiary Structure Prediction" Ch. 10:1–49 (1994).

(List continued on next page.)

*Primary Examiner*—John L. LeGuyader
*Assistant Examiner*—Jane Zara
(74) *Attorney, Agent, or Firm*—Robin M. Silva, Esq.; Renee M. Kosslak, Esq.; Dorsey & Whitney LLP

(57) ABSTRACT

The invention relates to novel non-naturally occurring cell surface receptor analogs, ligand analogs and nucleic acids encoding them. The invention further provides methods for screening of ligand analogs and bioactive agents capable of modulating the signaling activity of a non-naturally occurring cell surface receptor analog or capable of binding to a non-naturally occurring cell surface receptor analog.

5 Claims, 11 Drawing Sheets

OTHER PUBLICATIONS

Lasters, I., et al., "Dead–End Based Modeling Tools to Explore the Sequence Space That is Compatible with a Given Scaffold", *Jour. of Protein Chem.* vol. 16(5):449–452 (Jul. 1997).

Sun, S., et al., "Designing amino acid sequences to fold with good hydrophobic cores", *Protein Engg.* vol. 8(12):1205–1213 (1995).

Desmet, J. et al., "The dead–end elimination theorem and its use in protein side–chain positioning", *Nature* vol. 356:539–542 (Apr. 1992).

Bowie, J.U., et al., "Deciphering the Message in Protein Sequences: Tolerance to Amino Acid Substitutions", *Science* vol. 247:1306–1310 (Mar. 1990).

Desjarlais, J.R., et al., "De novo design of the hydrophobic cores of proteins", *Protein Science* 4:2006–2018 (1995).

Pabo, C., "Designing proteins and peptides", *Nature* vol. 1:200 (Jan. 1983).

Jones, D.T., "De novo protein design using pairwise potentials and a genetic algorithm", *Protein Science* 3:567–574 (1994).

Goldstein, R.F., "Efficient Rotamer Elimination Applied to Protein Side–Chains and Related Spin Glasses", *Biophys. Jour.* vol. 66:1335–1340 (May 1994).

Mayo et al., "First fully automatic design of a protein achieved by Caltech scientists", new press release (Oct. 1997).

Smith, C.K., et al., "Guidelines for Protein Design: The Energetics of β Sheet Side Chain Interactions", *Science* vol. 270:980–982 (Nov. 1995).

Regan, L., "Helix is a helix is a helix?", *Proc. Natl. Acad. Sci. USA* vol. 94:2796–2797 (Apr. 1997).

Muñoz, V., et al., "Intrinsic Secondary Structure Propensities of the Amino Acids, Using Statistical ϕ–ψ Matrices: Comparison with Experimental Scales", *Proteins* 20:301–311 (1994).

Stickle et al., "Bydrogen Bonding in Globular Proteins," Journal of Molecular Biology, 226:1143–1159 (1992).

Lasters et al., "Enhanced dead–end elimination in the search for the global minimum energy conformation of a collection of protein chains," Protein Engineering, 8(8):815–822 (1995).

Desmet et al., "Theoretical and Algorithmical Optimization of the Dead–End Elimination Theorem," *Proceedings of the Pacific Symposium on Biocomputing '97*, 122–133 (1997).

Holmes, "First–ever designer protein fits like a glove," New Scientist, IPC Magazines Limited, Oct. 11, 1997 (1997).

Muñoz, V., et al., "Helix design, prediction and stability", *Curr. Opin. in Biotech.* 6:382–386 (Aug. 1995).

Minor Jr., D.L., "Measurement of the β–sheet–forming propensities of amino acids", *Nature* vol. 367:660–663 (Feb. 1994).

Hellinga, H.W., et al., "Optimal sequence selection in proteins of known structure by simulated evolution", *Proc. Natl. Acad. Sci., USA* vol. 91:5803–5807 (Jun. 1994).

Bowie, J.U., et al., "A Method to Identify Protein Sequences that Fold into a Known Three–Dimensional Structure", *Science* vol. 253:164–170 (Jul. 1991).

Dalal, S., et al., "Protein alchemy: Changing β–sheet into α–helix", *Nature Struc. Biol.* vol. 4(7):548–552 (Jul. 1997).

Dahiyat, B.I., et al., "Proteins from Scratch", press digest email by *Science* (Sep. 26, 1997).

Berry, A., et al., "A quantitative methodology for the de novo design of proteins", *Protein Sci.* 3:1871–1882 (Oct. 1994).

Hellinga, H.W., "Rational protein design: Combining theory and experiment", *Proc. Natl. Acad. Sci, USA* vol. 94:10015–10017 (Sep. 1997).

Padmanabhan, S., et al., "Relative helix–forming tendencies of nonpolar amino acids", *Nature* vol. 344:268–270 (mar. 1990).

Connolly, M.L., "Solvent–Accessible Surfaces of Proteins and Nucleic Acids", *Science* vol. 221(4612):709–713 (Aug. 1983).

Eisenberg, D., et al., "Solvation energy in protein folding and binding", *Nature* vol. 319:199–203 (Jan. 1986).

Ponder, J.W., et al., "Use of Packing Criteria in the Enumeration of Allowed Sequences for Different Structural Classes", release by *Acad. Press Inc. (Londonl) Ltd.* pp.775–791 (1987).

Dahiyat, B.I., et al., "Automated design of the surface positions of protein helices", *Protein Science* 6:1–5 (Jun. 1997).

Harbury et al., "High–Resolution Protein Design with Backbone Freedom," *Science*, 282:1462–1467 (1998).

Kortemme et al., "Design of a 20–Amino Acid, Three–Stranded β–Sheet Protein," *Science*, 281:253–256 (1998).

Koehl et al., "De Novo Protein Design. I. In Search of Stability and Specificity," *J. Mol. Biol.*, 293:1161–1181 (1999).

Gordon et al. "Energy functions for protein design," *Curr. Opinion in Struct. Biol.*, 9:509–513 (1999).

Cornell et al., "A Second Generation Force Field for the Simulation of Proteins, Nucleic Acids, and Organic Molecules," *J. Am. Chem. Soc.*, 117:5179–5197 (1995).

Villegas et al., "Stabilization of proteins by rational design of α–helix stability using helix/coil transition theory," *Folding & Design*, 1(1):29–34 (1995).

Hurley et al., "Design and Structural Analysis of Alternative Hydrophobic Core Packing Arrangements in Bacteriophage T4 Lysozyme," *J. Mol. Biol.*, 224:1143–1159(1992).

Tuffery et al., "A New Approach to the Rapid Determination of Protein Side Chain Conformations," *J. of Biomolecular Struct. & Dynamics*, 8(6):1267–1289 (1991).

Brooks et al., "CHARMM: A Program for Macromolecular Energy, Minimization, and Dynamics Calculations," *J. of Computational Chemistry*, 4(2):187–217 (1983).

Rappé et al., "Charge Equilibration for Molecular Dynamics Simulations," *J. Phys. Chem.*, 95:3358–3363 (1991).

Mayo et al., "DREIDING: A Generic Force Field for Molecular Simulations," *J. Phys. Chem.*, 94:8897–8909 (1990).

Harbury et al., "Repacking protein cores with backbone freedom: Structure prediction for coiled coils," *Proc. Natl. Acad. Sci. USA*, 92:8408–8412 (1995).

Kono et al., "Energy Minimization Method Using Automata Network for Sequence and Side–Chain Conformation Prediction from Given Backbone Geometry," *Proteins: Structure, Function, and Genetics*, 19:244–255 (1994).

Lee et al., "Accurate prediction of the stability and activity effects of site–directed mutagenesis on a protein core," *Nature*, 352:448–451 (1991).

van Gunsteren et al., "Prediction of the Activity and Stability Effects of Site–directed Mutagenesis on a Protein Core," *J. Mol. Biol.*, 227:389–395 (1992).

Wesson et al., "Atomic solvation parameters applied to molecular dynamics of proteins in solution," *Protein Science,* 1:227–235 (1992).

Dahiyat et al., "Protein design automation," *Caltech Biology Annual Report,* 172 (1995).

Dahiyat et al., "Probing the Role of Specificity in Protein Design," *Caltech Biology Annual Report,* 160–161 (1996).

DeGrado, W., "Proteins from Scratch," *Science,* 278:80–81 (1997).

Dahiyat et al., "De Novo Protein Design: Fully Automated Sequence Selection," *Science,* 278:82–87 (1997).

Dahiyat et al., "Protein Design Automation," Meeting Abstract; Protein Science vol. 4, Suppl. 2, 83 (1995).

Dahiyat et al., "Protein design Automation," Poster Sessions, Protein Science vol. 5, Suppl. 1, 22–23 (1996).

* cited by examiner

TNFR trimer

```
Query:    1 APPPNLPDP 9

10        20        30        40        50        60
Query:   10 KFESKAALLAARGPEELLCFTERLEDLVCFWEEAASAGVGPGNYSFSYQLEDEPWKLCRL 69

Subject:  1 KFESKAALLAARGPEELLCFTERLEDLVCFWEEAASAGVGPGNYSFSYQLEDEPWKLCRL 60

PDA sites                                *        * * *              *
1ebp_d1_e2                                        F   F
1ebp_d1                                       F   F   F
1ebp_d2
1ebp_d12                                      F   F   F
1eer_d1                                           F   F
1eer_d1_211                                       F I F              I
1eer_d1_422                                   F   F   F
1eer_d2
1eer_d2_211
1eer_d2_422
1blw_d1                                           F   F
1blw_d1_211                                       F.  F
1blw_d1_422                                       F   F
1blw_d2
1blw_d2_211
1blw_d2_422 elbow_PDA     *    *  ***       *      *  *
1eer_ew            F
1eer_ew1      L          L      I
1eer_ew2           F W
1blw_ew       L    Y V          I
1blw_ew1      W    L I   L      L
1blw_ew2      L    W Y          I
1ebp_ew       Y    L YW  Y      I
1ebp_ew1      A    Y Y   Y      I Y
1ebp_ew2      Y    L IYW Y      I Y
1eer_17_ew1   K    M M          E
1eer_17_ew2        S K W        Q
1ebp_17_ew1   Q    R ND  R      E Y
```

FIGURE 8A

```
            70        80        90       100       110       120
Query:   70 HQAPTARGAVRFWCSLPTADTSSFVPLELRVTAASGAPRYHRVIHINEVVLLDAPVGLVA 129

Subject: 61 HQAPTARGAVRFWCSLPTADTSSFVPLELRVTAASGAPRYHRVIHINEVVLLDAPVGLVA 120

PDA sites               *  *    *      *  *  *       *               *  *
1ebp_d1_e2              I                            F
1ebp_d1                 I                   L        F
1ebp_d2
1ebp_d12                I                   L        F
1eer_d1                 I                            F
1eer_d1_211             Y              F             F
1eer_d1_422             I                   L
1eer_d2
1eer_d2_211
1eer_d2_422
1blw_d1                 I                   L        F
1blw_d1_211             I                   L        F
1blw_d1_422             I                   L        F
1blw_d2                                                             I V
1blw_d2_211
1blw_d2_422                                                         I elbow_PDA                                                     **
1eer_ew
1eer_ew1
1eer_ew2
1blw_ew
1blw_ew1                                             F
1blw_ew2
1ebp_ew                                              W
1ebp_ew1                                             Y
1ebp_ew2                                             W
1eer_17_ew1
1eer_17_ew2
1ebp_17_ew1                                          EM
```

FIGURE 8B

```
              130       140       150       160       170       180
Query:    130 RLADESGHVVLRWLPPPETPMTSHIRYEVDVSAGNGAGSVQRVEILEGRTECVLSNLRGR 189

Subject:  121 RLADESGHVVLRWLPPPETPMTSHIRYEVDVSAGNGAGSVQRVEILEGRTECVLSNLRGR 180

PDA sites           * * *         * * *           *         *
1ebp_d1_e2
1ebp_d1
1ebp_d2              I            F L I           L
1ebp_d12             I            F L I           L
1eer_d1
1eer_d1_211
1eer_d1_422
1eer_d2                           W I I
1eer_d2_211                       F I I
1eer_d2_422                       W L I
1blw_d1
1blw_d1_211
1blw_d1_422
1blw_d2             I I           F I I
1blw_d2_211
1blw_d2_422         I I           F I I elbow_PDA
1eer_ew
1eer_ew1
1eer_ew2
1blw_ew
1blw_ew1
1blw_ew2
1ebp_ew
1ebp_ew1
1ebp_ew2
1eer_17_ew1
1eer_17_ew2
1ebp_17_ew1
```

FIGURE 8C

```
              190       200       210       220
Query:    190 TRYTFAVRARMAEPSFGGFWSAWSEPVSLLT 220 PSDLD 225

Subject:  181 TRYTFAVRARMAEPSFGGFWSAWSEPVSLLT 211
```

| PDA sites    | * * * *   | *   | *   |
|---|---|---|---|
| 1ebp_d1_e2   |           |     | .   |
| 1ebp_d1      |           |     |     |
| 1ebp_d2      | I I       |     |     |
| 1ebp_d12     | I I       |     |     |
| 1eer_d1      |           |     |     |
| 1eer_d1_211  |           |     |     |
| 1eer_d1_422  |           |     |     |
| 1eer_d2      | F V       |     | F   |
| 1eer_d2_211  |   V       |     | F   |
| 1eer_d2_422  | F         |     | I   |
| 1blw_d1      |           |     |     |
| 1blw_d1_211  |           |     |     |
| 1blw_d1_422  |           |     |     |
| 1blw_d2      | I I I     |     | I   |
| 1blw_d2_211  |           |     |     |
| 1blw_d2_422  | I L I     |     |     |

| elbow_PDA   | * * | * |
|---|---|---|
| 1eer_ew     | W   |   |
| 1eer_ew1    |     | Y |
| 1eer_ew2    | WF  |   |
| 1blw_ew     | WI  |   |
| 1blw_ew1    | IY  |   |
| 1blw_ew2    | WI  |   |
| 1ebp_ew     | W   |   |
| 1ebp_ew1    | W   |   |
| 1ebp_ew2    | W   |   |
| 1eer_17_ew1 | ME  | Y |
| 1eer_17_ew2 | WE  |   |
| 1ebp_17_ew1 | N   |   |

FIGURE 8D

SEQUENCE LISTING

<160> NUMBER OF SEQ ID NOS: 37

<210> SEQ ID NO 1
<211> LENGTH: 225
<212> TYPE: PRT
<213> ORGANISM: Homo sapiens

<400> SEQUENCE: 1

```
Ala Pro Pro Pro Asn Leu Pro Asp Pro Lys Phe Glu Ser Lys Ala Ala
 1               5                  10                  15

Leu Leu Ala Ala Arg Gly Pro Glu Glu Leu Leu Cys Phe Thr Glu Arg
            20                  25                  30

Leu Glu Asp Leu Val Cys Phe Trp Glu Glu Ala Ala Ser Ala Gly Val
        35                  40                  45

Gly Pro Gly Asn Tyr Ser Phe Ser Tyr Gln Leu Glu Asp Glu Pro Trp
    50                  55                  60

Lys Leu Cys Arg Leu His Gln Ala Pro Thr Ala Arg Gly Ala Val Arg
65                  70                  75                  80

Phe Trp Cys Ser Leu Pro Thr Ala Asp Thr Ser Ser Phe Val Pro Leu
                85                  90                  95

Glu Leu Arg Val Thr Ala Ala Ser Gly Ala Pro Arg Tyr His Arg Val
            100                 105                 110

Ile His Ile Asn Glu Val Val Leu Leu Asp Ala Pro Val Gly Leu Val
        115                 120                 125

Ala Arg Leu Ala Asp Glu Ser Gly His Val Val Leu Arg Trp Leu Pro
    130                 135                 140

Pro Pro Glu Thr Pro Met Thr Ser His Ile Arg Tyr Glu Val Asp Val
145                 150                 155                 160

Ser Ala Gly Asn Gly Ala Gly Ser Val Gln Arg Val Glu Ile Leu Glu
                165                 170                 175

Gly Arg Thr Glu Cys Val Leu Ser Asn Leu Arg Gly Arg Thr Arg Tyr
            180                 185                 190

Thr Phe Ala Val Arg Ala Arg Met Ala Glu Pro Ser Phe Gly Gly Phe
        195                 200                 205

Trp Ser Ala Trp Ser Glu Pro Val Ser Leu Leu Thr Pro Ser Asp Leu
    210                 215                 220

Asp
225
```

<210> SEQ ID NO 2
<211> LENGTH: 211
<212> TYPE: PRT
<213> ORGANISM: Homo sapiens

<400> SEQUENCE: 2

```
Lys Phe Glu Ser Lys Ala Ala Leu Leu Ala Ala Arg Gly Pro Glu Glu
 1               5                  10                  15
```

```
Leu Leu Cys Phe Thr Glu Arg Leu Glu Asp Leu Val Cys Phe Trp Glu
             20                  25                  30

Glu Ala Ala Ser Ala Gly Val Gly Pro Gly Asn Tyr Ser Phe Ser Tyr
         35                  40                  45

Gln Leu Glu Asp Glu Pro Trp Lys Leu Cys Arg Leu His Gln Ala Pro
 50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
             85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Glu Thr Pro Met Thr Ser His
 130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
    210

<210> SEQ ID NO 3
<211> LENGTH: 212
<212> TYPE: PRT
<213> ORGANISM: Artificial Sequence
<220> FEATURE:
<223> OTHER INFORMATION: Description of Artificial Sequence: SYNTHETIC

<400> SEQUENCE: 3

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
             20                  25                  30

Glu Ala Ala Ser Ala Gly Val Gly Pro Gly Asn Phe Ser Phe Ser Phe
         35                  40                  45

Gln Leu Glu Asp Glu Pro Trp Lys Leu Cys Arg Leu His Gln Ala Pro
 50                  55                  60

Thr Ala Arg Gly Ala Ile Arg Ile Phe Trp Cys Ser Leu Pro Thr Ala
 65                  70                  75                  80

Asp Thr Ser Ser Phe Val Pro Leu Glu Leu Arg Val Thr Ala Ala Ser
             85                  90                  95

Gly Ala Pro Arg Phe His Arg Val Ile His Ile Asn Glu Val Val Leu
            100                 105                 110

Leu Asp Ala Pro Val Gly Leu Val Ala Arg Leu Ala Asp Glu Ser Gly
        115                 120                 125

His Val Val Leu Arg Trp Leu Pro Pro Glu Thr Pro Met Thr Ser
 130                 135                 140

His Ile Arg Tyr Glu Val Asp Val Ser Ala Gly Asn Gly Ala Gly Ser
145                 150                 155                 160
```

-continued

Val Gln Arg Val Glu Ile Leu Glu Gly Arg Thr Glu Cys Val Leu Ser
            165                 170                 175

Asn Leu Arg Gly Arg Thr Arg Tyr Thr Phe Ala Val Arg Ala Arg Met
            180                 185                 190

Ala Glu Pro Ser Phe Gly Gly Phe Trp Ser Ala Trp Ser Glu Pro Val
        195                 200                 205

Ser Leu Leu Thr
    210

<210> SEQ ID NO 4
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 4

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Phe Glu
            20                  25                  30

Glu Ala Ala Ser Ala Gly Val Gly Pro Gly Asn Phe Ser Phe Ser Phe
        35                  40                  45

Gln Leu Glu Asp Glu Pro Trp Lys Leu Cys Arg Leu His Gln Ala Pro
    50                  55                  60

Thr Ala Arg Gly Ala Ile Arg Phe Trp Cys Ser Leu Pro Thr Ala Asp
 65                 70                  75                  80

Thr Ser Ser Phe Val Pro Leu Glu Leu Arg Leu Thr Ala Ala Ser Gly
                85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Pro Glu Thr Pro Met Thr Ser His
    130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
    210

<210> SEQ ID NO 5
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 5

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
            20                  25                  30

```
Glu Ala Ala Ser Ala Gly Val Gly Pro Gly Asn Tyr Ser Phe Ser Tyr
            35                  40                  45

Gln Leu Glu Asp Glu Pro Trp Lys Leu Cys Arg Leu His Gln Ala Pro
 50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Ile Arg Trp Leu Pro Pro Glu Thr Pro Met Thr Ser His
            130                 135                 140

Ile Arg Phe Glu Leu Asp Ile Ser Ala Gly Asn Gly Ala Gly Ser Val
145                 150                 155                 160

Gln Arg Val Glu Leu Leu Glu Gly Arg Thr Glu Cys Val Leu Ser Asn
                165                 170                 175

Leu Arg Gly Arg Thr Arg Ile Thr Ile Ala Val Arg Ala Arg Met Ala
            180                 185                 190

Glu Pro Ser Phe Gly Gly Phe Trp Ser Ala Trp Ser Glu Pro Val Ser
            195                 200                 205

Leu Leu Thr
    210

<210> SEQ ID NO 6
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 6

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Phe Glu
            20                  25                  30

Glu Ala Ala Ser Ala Gly Val Gly Pro Gly Asn Phe Ser Phe Ser Phe
            35                  40                  45

Gln Leu Glu Asp Glu Pro Trp Lys Leu Cys Arg Leu His Gln Ala Pro
 50                  55                  60

Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Leu Thr Ala Ala Ser Gly
                 85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Ile Arg Trp Leu Pro Pro Glu Thr Pro Met Thr Ser His
            130                 135                 140

Ile Arg Phe Glu Leu Asp Ile Ser Ala Gly Asn Gly Ala Gly Ser Val
145                 150                 155                 160

Gln Arg Val Glu Leu Leu Glu Gly Arg Thr Glu Cys Val Leu Ser Asn
                165                 170                 175
```

```
Leu Arg Gly Arg Thr Arg Ile Thr Ile Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
    210

<210> SEQ ID NO 7
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 7

Lys Phe Glu Ser Lys Ala Ala Leu Leu Ala Ala Arg Gly Pro Glu Glu
  1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Phe Ser Phe Ser Phe
            35                  40                  45

Gln Leu Glu Asp Glu Pro Trp Lys Leu Cys Arg Leu His Gln Ala Pro
        50                  55                  60

Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Glu Thr Pro Met Thr Ser His
    130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
    210

<210> SEQ ID NO 8
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 8

Lys Phe Glu Ser Lys Ala Ala Leu Leu Ala Ala Arg Gly Pro Glu Glu
  1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Phe Ser Ile Ser Phe
```

```
                    35                  40                  45
Gln Leu Glu Asp Glu Pro Trp Lys Leu Cys Arg Ile His Gln Ala Pro
         50                  55                  60

Thr Ala Arg Gly Ala Tyr Arg Phe Trp Cys Ser Leu Pro Thr Ala Asp
 65                  70                  75                  80

Thr Ser Ser Phe Val Pro Phe Glu Leu Arg Val Thr Ala Ala Ser Gly
                 85                  90                  95

Ala Pro Arg Phe His Arg Val Ile His Ile Asn Glu Val Val Leu Leu
                100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
210

<210> SEQ ID NO 9
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 9

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Phe Glu
                20                  25                  30

Glu Ala Ala Ser Ala Gly Val Gly Pro Gly Asn Phe Ser Phe Ser Phe
            35                  40                  45

Gln Leu Glu Asp Glu Pro Trp Lys Leu Cys Arg Leu His Gln Ala Pro
         50                  55                  60

Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Leu Thr Ala Ala Ser Gly
                 85                  90                  95

Ala Pro Arg Tyr His Arg Val Ile His Ile Asn Glu Val Val Leu Leu
                100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
```

```
            180                 185                 190
Glu Pro Ser Phe Gly Gly Phe Trp Ser Ala Trp Ser Glu Pro Val Ser
        195                 200                 205

Leu Leu Thr
    210

<210> SEQ ID NO 10
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 10

Lys Phe Glu Ser Lys Ala Ala Leu Leu Ala Ala Arg Gly Pro Glu Glu
  1               5                  10                  15

Leu Leu Cys Phe Thr Glu Arg Leu Glu Asp Leu Val Cys Phe Trp Glu
                 20                  25                  30

Glu Ala Ala Ser Ala Gly Val Gly Pro Gly Asn Tyr Ser Phe Ser Tyr
             35                  40                  45

Gln Leu Glu Asp Glu Pro Trp Lys Leu Cys Arg Leu His Gln Ala Pro
     50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Pro Glu Thr Pro Met Thr Ser His
    130                 135                 140

Ile Arg Trp Glu Ile Asp Ile Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Phe Thr Val Ala Val Arg Ala Arg Met Ala
            180                 185                 190

Glu Pro Ser Phe Gly Gly Phe Trp Ser Ala Trp Ser Glu Pro Val Ser
        195                 200                 205

Phe Leu Thr
    210

<210> SEQ ID NO 11
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 11

Lys Phe Glu Ser Lys Ala Ala Leu Leu Ala Ala Arg Gly Pro Glu Glu
  1               5                  10                  15

Leu Leu Cys Phe Thr Glu Arg Leu Glu Asp Leu Val Cys Phe Trp Glu
                 20                  25                  30

Glu Ala Ala Ser Ala Gly Val Gly Pro Gly Asn Tyr Ser Phe Ser Tyr
             35                  40                  45
```

-continued

```
Gln Leu Glu Asp Glu Pro Trp Lys Leu Cys Arg Leu His Gln Ala Pro
 50                  55                  60
Thr Ala Arg Gly Ala Val Arg Phe Trp Cys Ser Leu Pro Thr Ala Asp
 65                  70                  75                  80
Thr Ser Ser Phe Val Pro Leu Glu Leu Arg Val Thr Ala Ala Ser Gly
                 85                  90                  95
Ala Pro Arg Tyr His Arg Val Ile His Ile Asn Glu Val Val Leu Leu
                100                 105                 110
Asp Ala Pro Val Gly Leu Val Ala Arg Leu Ala Asp Glu Ser Gly His
            115                 120                 125
Val Val Leu Arg Trp Leu Pro Pro Glu Thr Pro Met Thr Ser His
130                 135                 140
Ile Arg Phe Glu Ile Asp Ile Ser Ala Gly Asn Gly Ala Gly Ser Val
145                 150                 155                 160
Gln Arg Val Glu Ile Leu Glu Gly Arg Thr Glu Cys Val Leu Ser Asn
                165                 170                 175
Leu Arg Gly Arg Thr Arg Tyr Thr Val Ala Val Arg Ala Arg Met Ala
            180                 185                 190
Glu Pro Ser Phe Gly Gly Phe Trp Ser Ala Trp Ser Glu Pro Val Ser
        195                 200                 205
Phe Leu Thr
210

<210> SEQ ID NO 12
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 12

Lys Phe Glu Ser Lys Ala Ala Leu Leu Ala Ala Arg Gly Pro Glu Glu
 1               5                  10                  15
Leu Leu Cys Phe Thr Glu Arg Leu Glu Asp Leu Val Cys Phe Trp Glu
             20                  25                  30
Glu Ala Ala Ser Ala Gly Val Gly Pro Gly Asn Tyr Ser Phe Ser Tyr
         35                  40                  45
Gln Leu Glu Asp Glu Pro Trp Lys Leu Cys Arg Leu His Gln Ala Pro
 50                  55                  60
Thr Ala Arg Gly Ala Val Arg Phe Trp Cys Ser Leu Pro Thr Ala Asp
 65                  70                  75                  80
Thr Ser Ser Phe Val Pro Leu Glu Leu Arg Val Thr Ala Ala Ser Gly
                 85                  90                  95
Ala Pro Arg Tyr His Arg Val Ile His Ile Asn Glu Val Val Leu Leu
                100                 105                 110
Asp Ala Pro Val Gly Leu Val Ala Arg Leu Ala Asp Glu Ser Gly His
            115                 120                 125
Val Val Leu Arg Trp Leu Pro Pro Glu Thr Pro Met Thr Ser His
130                 135                 140
Ile Arg Trp Glu Leu Asp Ile Ser Ala Gly Asn Gly Ala Gly Ser Val
145                 150                 155                 160
Gln Arg Val Glu Ile Leu Glu Gly Arg Thr Glu Cys Val Leu Ser Asn
                165                 170                 175
Leu Arg Gly Arg Thr Arg Phe Thr Phe Ala Val Arg Ala Arg Met Ala
            180                 185                 190
```

-continued

Glu Pro Ser Phe Gly Gly Phe Trp Ser Ala Trp Ser Glu Pro Val Ser
            195                 200                 205

Ile Leu Thr
    210

<210> SEQ ID NO 13
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 13

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Phe Ser Phe Ser Phe
            35                  40                  45

Gln Leu Glu Asp Glu Pro Trp Lys Leu Cys Arg Leu His Gln Ala Pro
        50                  55                  60

Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Leu Thr Ala Ala Ser Gly
                 85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Glu Thr Pro Met Thr Ser His
    130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
        195                 200                 205

Leu Leu Thr
    210

<210> SEQ ID NO 14
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 14

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Phe Ser Phe Ser Phe
            35                  40                  45

Gln Leu Glu Asp Glu Pro Trp Lys Leu Cys Arg Leu His Gln Ala Pro
        50                  55                  60

-continued

```
Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Leu Thr Ala Ala Ser Gly
             85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
            195                 200                 205

Leu Leu Thr
210

<210> SEQ ID NO 15
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 15

Lys Phe Glu Ser Lys Ala Ala Leu Leu Ala Ala Arg Gly Pro Glu Glu
  1               5                  10                  15

Leu Leu Cys Phe Thr Glu Arg Leu Glu Asp Leu Val Cys Phe Trp Glu
             20                  25                  30

Glu Ala Ala Ser Ala Gly Val Gly Pro Gly Asn Phe Ser Phe Ser Phe
         35                  40                  45

Gln Leu Glu Asp Glu Pro Trp Lys Leu Cys Arg Leu His Gln Ala Pro
 50                  55                  60

Thr Ala Arg Gly Ala Ile Arg Phe Trp Cys Ser Leu Pro Thr Ala Asp
 65                  70                  75                  80

Thr Ser Ser Phe Val Pro Leu Glu Leu Arg Leu Thr Ala Ala Ser Gly
             85                  90                  95

Ala Pro Arg Phe His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Trp Ser Glu Pro Val Ser
            195                 200                 205
```

Leu Leu Thr
        210

<210> SEQ ID NO 16
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 16

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Tyr Ser Phe Ser Tyr
            35                  40                  45

Gln Leu Glu Asp Glu Pro Trp Lys Leu Cys Arg Leu His Gln Ala Pro
        50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Leu Leu
            100                 105                 110

Asp Ala Pro Val Gly Ile Val Arg Leu Ala Asp Glu Ser Gly His
        115                 120                 125

Ile Val Ile Arg Trp Leu Pro Pro Pro Glu Thr Pro Met Thr Ser His
130                 135                 140

Ile Arg Phe Glu Ile Asp Ile Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Ile Thr Ile Ala Ile Arg Ala Arg Met Ala
            180                 185                 190

Glu Pro Ser Phe Gly Gly Phe Trp Ser Ala Trp Ser Glu Pro Val Ser
        195                 200                 205

Ile Leu Thr
       210

<210> SEQ ID NO 17
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 17

Lys Phe Glu Ser Lys Ala Ala Leu Leu Ala Ala Arg Gly Pro Glu Glu
 1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Tyr Ser Phe Ser Tyr
            35                  40                  45

Gln Leu Glu Asp Glu Pro Trp Lys Leu Cys Arg Leu His Gln Ala Pro
        50                  55                  60

Thr Ala Arg Gly Ala Val Arg Phe Trp Cys Ser Leu Pro Thr Ala Asp

```
                 65                  70                  75                  80
Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Leu Leu
               100                 105                 110

Asp Ala Pro Val Gly Ile Val Ala Arg Leu Ala Asp Glu Ser Gly His
               115                 120                 125

Ile Val Ile Arg Trp Leu Pro Pro Glu Thr Pro Met Thr Ser His
130                 135                 140

Ile Arg Phe Glu Ile Asp Ile Ser Ala Gly Asn Gly Ala Gly Ser Val
145                 150                 155                 160

Gln Arg Val Glu Ile Leu Glu Gly Arg Thr Glu Cys Val Leu Ser Asn
               165                 170                 175

Leu Arg Gly Arg Thr Arg Ile Thr Leu Ala Ile Arg Ala Arg Met Ala
               180                 185                 190

Glu Pro Ser Phe Gly Gly Phe Trp Ser Ala Trp Ser Glu Pro Val Ser
               195                 200                 205

Leu Leu Thr
210

<210> SEQ ID NO 18
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 18

Lys Phe Glu Ser Lys Ala Ala Phe Leu Ala Ala Arg Gly Pro Glu Glu
1               5                  10                  15

Leu Leu Cys Phe Thr Glu Arg Leu Glu Asp Leu Val Cys Phe Trp Glu
                20                  25                  30

Glu Ala Ala Ser Ala Gly Val Gly Pro Gly Asn Tyr Ser Phe Ser Tyr
                35                  40                  45

Gln Leu Glu Asp Glu Pro Trp Lys Leu Cys Arg Leu His Gln Ala Pro
50                  55                  60

Thr Ala Arg Gly Ala Val Arg Phe Trp Cys Ser Leu Pro Thr Ala Asp
65                  70                  75                  80

Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Leu Leu
               100                 105                 110

Asp Ala Pro Val Gly Leu Val Ala Arg Leu Ala Asp Glu Ser Gly His
               115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
               165                 170                 175

Leu Arg Gly Arg Thr Arg Tyr Thr Phe Ala Val Arg Ala Arg Met Ala
               180                 185                 190

Glu Pro Ser Phe Gly Trp Phe Trp Ser Ala Trp Ser Glu Pro Val Ser
               195                 200                 205

Leu Leu Thr
```

<210> SEQ ID NO 19
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 19

```
Lys Phe Glu Ser Lys Leu Ala Leu Ala Ala Arg Gly Pro Glu Glu
  1               5                  10                  15

Leu Leu Cys Leu Thr Glu Arg Leu Glu Asp Leu Ile Cys Phe Trp Glu
                 20                  25                  30

Glu Ala Ala Ser Ala Gly Val Gly Pro Gly Asn Tyr Ser Phe Ser Tyr
             35                  40                  45

Gln Leu Glu Asp Glu Pro Trp Lys Leu Cys Arg Leu His Gln Ala Pro
         50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Glu Thr Pro Met Thr Ser His
    130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Phe Trp Ser Ala Tyr Ser Glu Pro Val Ser
        195                 200                 205

Leu Leu Thr
    210
```

<210> SEQ ID NO 20
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 20

```
Lys Phe Glu Ser Lys Ala Ala Phe Leu Trp Ala Arg Gly Pro Glu Glu
  1               5                  10                  15

Leu Leu Cys Phe Thr Glu Arg Leu Glu Asp Leu Val Cys Phe Trp Glu
                 20                  25                  30

Glu Ala Ala Ser Ala Gly Val Gly Pro Gly Asn Tyr Ser Phe Ser Tyr
             35                  40                  45

Gln Leu Glu Asp Glu Pro Trp Lys Leu Cys Arg Leu His Gln Ala Pro
         50                  55                  60

Thr Ala Arg Gly Ala Val Arg Phe Trp Cys Ser Leu Pro Thr Ala Asp
 65                  70                  75                  80
```

```
Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
            165                 170                 175

Leu Arg Gly Arg Thr Arg Tyr Thr Phe Ala Val Arg Ala Arg Met Ala
            180                 185                 190

Glu Pro Ser Phe Gly Gly Trp Phe Ser Ala Trp Ser Glu Pro Val Ser
            195                 200                 205

Leu Leu Thr
    210

<210> SEQ ID NO 21
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 21

Lys Leu Glu Ser Lys Ala Ala Tyr Leu Val Ala Arg Gly Pro Glu Glu
  1               5                  10                  15

Leu Leu Cys Phe Thr Glu Arg Leu Glu Asp Leu Ile Cys Phe Trp Glu
             20                  25                  30

Glu Ala Ala Ser Ala Gly Val Gly Pro Gly Asn Tyr Ser Phe Ser Tyr
            35                  40                  45

Gln Leu Glu Asp Glu Pro Trp Lys Leu Cys Arg Leu His Gln Ala Pro
 50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
            165                 170                 175

Leu Arg Gly Arg Thr Arg Tyr Thr Phe Ala Val Arg Ala Arg Met Ala
            180                 185                 190

Glu Pro Ser Phe Gly Gly Trp Ile Ser Ala Trp Ser Glu Pro Val Ser
            195                 200                 205

Leu Leu Thr
    210
```

```
<210> SEQ ID NO 22
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 22

Lys Trp Glu Ser Lys Leu Ala Ile Leu Ala Ala Arg Gly Pro Glu Glu
 1               5                  10                  15

Leu Leu Cys Leu Thr Glu Arg Leu Glu Asp Leu Leu Cys Phe Trp Glu
            20                  25                  30

Glu Ala Ala Ser Ala Gly Val Gly Pro Gly Asn Tyr Ser Phe Ser Tyr
        35                  40                  45

Gln Leu Glu Asp Glu Pro Trp Lys Leu Cys Arg Leu His Gln Ala Pro
    50                  55                  60

Thr Ala Arg Gly Ala Val Arg Phe Trp Cys Ser Leu Pro Thr Ala Asp
65                  70                  75                  80

Thr Ser Ser Phe Val Pro Leu Glu Leu Arg Val Thr Ala Ala Ser Gly
                85                  90                  95

Ala Pro Arg Tyr His Arg Val Ile His Ile Asn Glu Val Val Phe Leu
            100                 105                 110

Asp Ala Pro Val Gly Leu Val Ala Arg Leu Ala Asp Glu Ser Gly His
        115                 120                 125

Val Val Leu Arg Trp Leu Pro Pro Pro Glu Thr Pro Met Thr Ser His
    130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Ile Tyr Ser Ala Trp Ser Glu Pro Val Ser
        195                 200                 205

Leu Leu Thr
    210

<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 23

Lys Leu Glu Ser Lys Ala Ala Trp Leu Tyr Ala Arg Gly Pro Glu Glu
 1               5                  10                  15

Leu Leu Cys Phe Thr Glu Arg Leu Glu Asp Leu Ile Cys Phe Trp Glu
            20                  25                  30

Glu Ala Ala Ser Ala Gly Val Gly Pro Gly Asn Tyr Ser Phe Ser Tyr
        35                  40                  45

Gln Leu Glu Asp Glu Pro Trp Lys Leu Cys Arg Leu His Gln Ala Pro
    50                  55                  60

Thr Ala Arg Gly Ala Val Arg Phe Trp Cys Ser Leu Pro Thr Ala Asp
65                  70                  75                  80

Thr Ser Ser Phe Val Pro Leu Glu Leu Arg Val Thr Ala Ala Ser Gly
                85                  90                  95
```

```
Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
            130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
            165                 170                 175

Leu Arg Gly Arg Thr Arg Tyr Thr Phe Ala Val Arg Ala Arg Met Ala
            180                 185                 190

Glu Pro Ser Phe Gly Gly Trp Ile Ser Ala Trp Ser Glu Pro Val Ser
            195                 200                 205

Leu Leu Thr
    210

<210> SEQ ID NO 24
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 24

Lys Tyr Glu Ser Lys Leu Ala Leu Tyr Trp Ala Arg Gly Pro Glu Glu
1               5                   10                  15

Leu Leu Cys Tyr Thr Glu Arg Leu Glu Asp Leu Ile Cys Phe Trp Glu
            20                  25                  30

Glu Ala Ala Ser Ala Gly Val Gly Pro Gly Asn Tyr Ser Phe Ser Tyr
            35                  40                  45

Gln Leu Glu Asp Glu Pro Trp Lys Leu Cys Arg Leu His Gln Ala Pro
    50                  55                  60

Thr Ala Arg Gly Ala Val Arg Phe Trp Cys Ser Leu Pro Thr Ala Asp
65                  70                  75                  80

Thr Ser Ser Phe Val Pro Leu Glu Leu Arg Val Thr Ala Ala Ser Gly
            85                  90                  95

Ala Pro Arg Tyr His Arg Val Ile His Ile Asn Glu Val Val Trp Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
            130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
            165                 170                 175

Leu Arg Gly Arg Thr Arg Tyr Thr Phe Ala Val Arg Ala Arg Met Ala
            180                 185                 190

Glu Pro Ser Phe Gly Gly Trp Trp Ser Ala Trp Ser Glu Pro Val Ser
            195                 200                 205

Leu Leu Thr
    210

<210> SEQ ID NO 25
```

<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 25

```
Lys Ala Glu Ser Lys Tyr Ala Leu Tyr Ala Arg Gly Pro Glu Glu
  1               5                  10                  15

Leu Leu Cys Tyr Thr Glu Arg Leu Glu Asp Leu Ile Cys Tyr Trp Glu
             20                  25                  30

Glu Ala Ala Ser Ala Gly Val Gly Pro Gly Asn Tyr Ser Phe Ser Tyr
             35                  40                  45

Gln Leu Glu Asp Glu Pro Trp Lys Leu Cys Arg Leu His Gln Ala Pro
     50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Tyr Leu
                100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
        130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Trp Trp Ser Ala Trp Ser Glu Pro Val Ser
            195                 200                 205

Leu Leu Thr
    210
```

<210> SEQ ID NO 26
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 26

```
Lys Tyr Glu Ser Lys Leu Ala Ile Tyr Trp Ala Arg Gly Pro Glu Glu
  1               5                  10                  15

Leu Leu Cys Tyr Thr Glu Arg Leu Glu Asp Leu Ile Cys Tyr Trp Glu
             20                  25                  30

Glu Ala Ala Ser Ala Gly Val Gly Pro Gly Asn Tyr Ser Phe Ser Tyr
             35                  40                  45

Gln Leu Glu Asp Glu Pro Trp Lys Leu Cys Arg Leu His Gln Ala Pro
     50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Leu Trp
```

```
                100                 105                 110
Asp Ala Pro Val Gly Leu Val Ala Arg Leu Ala Asp Glu Ser Gly His
            115                 120                 125
Val Val Leu Arg Trp Leu Pro Pro Glu Thr Pro Met Thr Ser His
        130                 135                 140
Ile Arg Tyr Glu Val Asp Val Ser Ala Gly Asn Gly Ala Gly Ser Val
145                 150                 155                 160
Gln Arg Val Glu Ile Leu Glu Gly Arg Thr Glu Cys Val Leu Ser Asn
                165                 170                 175
Leu Arg Gly Arg Thr Arg Tyr Thr Phe Ala Val Arg Ala Arg Met Ala
            180                 185                 190
Glu Pro Ser Phe Gly Gly Trp Trp Ser Ala Trp Ser Glu Pro Val Ser
                195                 200                 205
Leu Leu Thr
    210

<210> SEQ ID NO 27
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 27

Lys Lys Glu Ser Lys Met Ala Met Leu Ala Ala Arg Gly Pro Glu Glu
1               5                   10                  15
Leu Leu Cys Phe Thr Glu Arg Leu Glu Asp Leu Glu Cys Phe Trp Glu
                20                  25                  30
Glu Ala Ala Ser Ala Gly Val Gly Pro Gly Asn Tyr Ser Phe Ser Tyr
            35                  40                  45
Gln Leu Glu Asp Glu Pro Trp Lys Leu Cys Arg Leu His Gln Ala Pro
        50                  55                  60
Thr Ala Arg Gly Ala Val Arg Phe Trp Cys Ser Leu Pro Thr Ala Asp
65                  70                  75                  80
Thr Ser Ser Phe Val Pro Leu Glu Leu Arg Val Thr Ala Ala Ser Gly
                85                  90                  95
Ala Pro Arg Tyr His Arg Val Ile His Ile Asn Glu Val Val Leu Leu
                100                 105                 110
Asp Ala Pro Val Gly Leu Val Ala Arg Leu Ala Asp Glu Ser Gly His
            115                 120                 125
Val Val Leu Arg Trp Leu Pro Pro Glu Thr Pro Met Thr Ser His
        130                 135                 140
Ile Arg Tyr Glu Val Asp Val Ser Ala Gly Asn Gly Ala Gly Ser Val
145                 150                 155                 160
Gln Arg Val Glu Ile Leu Glu Gly Arg Thr Glu Cys Val Leu Ser Asn
                165                 170                 175
Leu Arg Gly Arg Thr Arg Tyr Thr Phe Ala Val Arg Ala Arg Met Ala
            180                 185                 190
Glu Pro Ser Phe Gly Gly Met Glu Ser Ala Tyr Ser Glu Pro Val Ser
                195                 200                 205
Leu Leu Thr
    210

<210> SEQ ID NO 28
<211> LENGTH: 211
<212> TYPE: PRT
```

<213> ORGANISM: Artificial Sequence
<220> FEATURE:
<223> OTHER INFORMATION: Description of Artificial Sequence: SYNTHETIC

<400> SEQUENCE: 28

```
Lys Phe Glu Ser Lys Ser Ala Lys Leu Trp Ala Arg Gly Pro Glu Glu
  1               5                  10                  15

Leu Leu Cys Phe Thr Glu Arg Leu Glu Asp Leu Gln Cys Phe Trp Glu
             20                  25                  30

Glu Ala Ala Ser Ala Gly Val Gly Pro Gly Asn Tyr Ser Phe Ser Tyr
         35                  40                  45

Gln Leu Glu Asp Glu Pro Trp Lys Leu Cys Arg Leu His Gln Ala Pro
     50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Leu Leu
            100                 105                 110

Asp Ala Pro Val Gly Leu Val Ala Arg Leu Ala Asp Glu Ser Gly His
            115                 120                 125

Val Val Leu Arg Trp Leu Pro Pro Glu Thr Pro Met Thr Ser His
130                 135                 140

Ile Arg Tyr Glu Val Asp Val Ser Ala Gly Asn Gly Ala Gly Ser Val
145                 150                 155                 160

Gln Arg Val Glu Ile Leu Glu Gly Arg Thr Glu Cys Val Leu Ser Asn
                165                 170                 175

Leu Arg Gly Arg Thr Arg Tyr Thr Phe Ala Val Arg Ala Arg Met Ala
            180                 185                 190

Glu Pro Ser Phe Gly Gly Trp Glu Ser Ala Trp Ser Glu Pro Val Ser
            195                 200                 205

Leu Leu Thr
    210
```

<210> SEQ ID NO 29
<211> LENGTH: 211
<212> TYPE: PRT
<213> ORGANISM: Artificial Sequence
<220> FEATURE:
<223> OTHER INFORMATION: Description of Artificial Sequence: SYNTHETIC

<400> SEQUENCE: 29

```
Lys Gln Glu Ser Lys Arg Ala Leu Asn Asp Ala Arg Gly Pro Glu Glu
  1               5                  10                  15

Leu Leu Cys Arg Thr Glu Arg Leu Glu Asp Leu Glu Cys Tyr Trp Glu
             20                  25                  30

Glu Ala Ala Ser Ala Gly Val Gly Pro Gly Asn Tyr Ser Phe Ser Tyr
         35                  40                  45

Gln Leu Glu Asp Glu Pro Trp Lys Leu Cys Arg Leu His Gln Ala Pro
     50                  55                  60

Thr Ala Arg Gly Ala Val Arg Phe Trp Cys Ser Leu Pro Thr Ala Asp
 65                  70                  75                  80

Thr Ser Ser Phe Val Pro Leu Glu Leu Arg Val Thr Ala Ala Ser Gly
                 85                  90                  95

Ala Pro Arg Tyr His Arg Val Ile His Ile Asn Glu Val Val Glu Met
            100                 105                 110
```

```
Asp Ala Pro Val Gly Leu Val Ala Arg Leu Ala Asp Glu Ser Gly His
        115                 120                 125
Val Val Leu Arg Trp Leu Pro Pro Glu Thr Pro Met Thr Ser His
    130                 135                 140
Ile Arg Tyr Glu Val Asp Val Ser Ala Gly Asn Gly Ala Gly Ser Val
145                 150                 155                 160
Gln Arg Val Glu Ile Leu Glu Gly Arg Thr Glu Cys Val Leu Ser Asn
                165                 170                 175
Leu Arg Gly Arg Thr Arg Tyr Thr Phe Ala Val Arg Ala Arg Met Ala
            180                 185                 190
Glu Pro Ser Phe Gly Gly Asn Trp Ser Ala Trp Ser Glu Pro Val Ser
        195                 200                 205
Leu Leu Thr
    210

<210> SEQ ID NO 30
<211> LENGTH: 5
<212> TYPE: PRT
<213> ORGANISM: Unknown Organism
<220> FEATURE:
<221> NAME/KEY: UNSURE
<222> LOCATION: (3)
<223> OTHER INFORMATION: Xaa at position 3 can be any amino acid
<220> FEATURE:
<223> OTHER INFORMATION: Description of Unknown Organism:  cytokine
      receptor motif found in many species

<400> SEQUENCE: 30

Trp Ser Xaa Trp Ser
1               5

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: SYNTHETIC

<400> SEQUENCE: 31

Arg Met Glu Lys Leu Glu Gln Lys Val Lys Glu Leu Leu Arg Lys Asn
1               5                   10                  15
Glu Arg Leu Glu Glu Glu Val Glu Arg Leu Lys Gln Leu Val Gly Glu
            20                  25                  30
Arg

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: SYNTHETIC

<400> SEQUENCE: 32

Ala Ala Leu Glu Ser Glu Val Ser Ala Leu Glu Ser Glu Val Ala Ser
1               5                   10                  15
Leu Glu Ser Glu Val Ala Ala Leu
            20

<210> SEQ ID NO 33
<211> LENGTH: 24
<212> TYPE: PRT
<213> ORGANISM: Artificial Sequence
<220> FEATURE:
```

<223> OTHER INFORMATION: Description of Artificial Sequence: SYNTHETIC

<400> SEQUENCE: 33

```
Leu Ala Ala Val Lys Ser Lys Leu Ser Ala Val Lys Ser Lys Leu Ala
 1               5                   10                  15

Ser Val Lys Ser Lys Leu Ala Ala
            20
```

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: SYNTHETIC

<400> SEQUENCE: 34

```
Gly Ser Gly Gly Ser
 1               5
```

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: SYNTHETIC

<400> SEQUENCE: 35

```
Gly Gly Gly Gly Ser
 1               5
```

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: SYNTHETIC

<400> SEQUENCE: 36

```
Gly Gly Gly Ser
 1
```

<210> SEQ ID NO 37
<211> LENGTH: 249
<212> TYPE: PRT
<213> ORGANISM: Artificial Sequence
<220> FEATURE:
<223> OTHER INFORMATION: Description of Artificial Sequence:  synthetic

<400> SEQUENCE: 37

```
Lys Phe Glu Ser Lys Ala Ala Leu Leu Ala Ala Arg Gly Pro Glu Glu
 1               5                   10                  15

Leu Leu Cys Phe Thr Glu Arg Leu Glu Asp Leu Val Cys Phe Phe Glu
            20                  25                  30

Glu Ala Ala Ser Ala Gly Val Gly Pro Gly Asn Phe Ser Phe Ser Phe
        35                  40                  45

Gln Leu Glu Asp Glu Pro Trp Lys Leu Cys Arg Leu His Gln Ala Pro
    50                  55                  60

Thr Ala Arg Gly Ala Ile Arg Phe Trp Cys Ser Leu Pro Thr Ala Asp
65                  70                  75                  80

Thr Ser Ser Phe Val Pro Leu Glu Leu Arg Leu Thr Ala Ala Ser Gly
                85                  90                  95

Ala Pro Arg Phe His Arg Val Ile His Ile Asn Glu Val Val Leu Leu
            100                 105                 110
```

```
Asp Ala Pro Val Gly Leu Val Ala Arg Leu Ala Asp Glu Ser Gly His
        115                 120                 125

Val Val Ile Arg Trp Leu Pro Pro Glu Thr Pro Met Thr Ser His
        130                 135                 140

Ile Arg Phe Glu Leu Asp Ile Ser Ala Gly Asn Gly Ala Gly Ser Val
145                 150                 155                 160

Gln Arg Val Glu Leu Leu Glu Gly Arg Thr Glu Cys Val Leu Ser Asn
                165                 170                 175

Leu Arg Gly Arg Thr Arg Ile Thr Ile Ala Val Arg Ala Arg Met Ala
                180                 185                 190

Glu Pro Ser Phe Gly Gly Phe Trp Ser Ala Trp Ser Glu Pro Val Ser
        195                 200                 205

Leu Leu Thr Gly Gly Gly Gly Ser Arg Met Glu Lys Leu Glu Gln Lys
        210                 215                 220

Val Lys Glu Leu Leu Arg Lys Asn Glu Arg Leu Glu Glu Glu Val Glu
225                 230                 235                 240

Arg Leu Lys Gln Leu Val Gly Glu Arg
                245
```

STRUCTURE-BASED SCREENING TECHNIQUES FOR DRUG DISCOVERY

This application is a continuing application of U.S.S.N.s 60/120,009, filed Feb. 11, 1999 and of 60/131,674, filed Apr. 29, 1999, each of which are expressly incorporated by reference.

FIELD OF THE INVENTION

The invention relates to novel non-naturally occurring cell surface receptor analogs, ligand analogs and nucleic acids encoding them. The invention further provides methods for screening of ligand analogs and bioactive agents capable of modulating the signaling activity of a non-naturally occurring cell surface receptor analog or capable of binding to a non-naturally occurring cell surface receptor analog.

BACKGROUND OF THE INVENTION

Cytokines and hormones are secreted proteins that bind to cell surface receptors and activate cellular differentiation and proliferation through a cascade of intracellular signaling events. They include insulin, erythropoietin (EPO), granulocyte colony stimulating factor (GCS F), thrombopoietin (TPO), human growth hormone (hGH), vascular endothelial growth factor (VEGF), angiostatin, endostatin, insulin, the interleukins, and the interferons. In general, each cytokine has a specific cell-surface receptor. These receptors comprise three major domains: an extracellular portion that binds the cytokine, a transmembrane domain to anchor the receptor in the membrane, and an intracellular signaling domain that is activated by cytokine binding.

Cytokines generally have at least two binding sites, and sometimes three, for the receptors. Monomeric receptors are brought together by cytokine binding, to result in the formation of a receptor oligomer. This oligomer is the biologically active form and is necessary for a variety of intracellular receptor signaling events.

From a commercial perspective, cytokines are used to treat millions of patients for anemia, cancer, diabetes, neurological and growth disorders. However, cytokines are generally large molecules that must be administered by intravenous or subcutaneous injection. Accordingly, the pharmaceutical industry has been highly motivated to develop small molecule replacement that can be taken orally. Thus, there is enormous commercial interest in finding cytokine-mimetic drugs that could eliminate the need for injection and lower the cost of producing the recombinant proteins.

However, a variety of technical barriers have prevented the discovery and commercialization of small molecule mimics for cytokines. The development of small molecule cytokine mimics is blocked by the difficulty in reconstituting the biologically relevant receptor structure, a precisely oriented receptor oligomer. So far it has not been possible to reconstitute the active receptor oligomer for use in in vitro drug screening assays, aiming to isolate cytokine mimetics. Current screening approaches utilize receptor molecules in random orientations, not as functional dimers or trimers, thereby screening for receptor affinity rather than activity. Cell-based assays have recently been developed that present receptors in a 'natural' manner however, these assays are difficult to use and limited in screening power for high throughput screening.

De novo protein design has received considerable attention recently, and significant advances have been made toward the goal of producing stable, well-folded proteins with novel sequences. Efforts to design proteins rely on knowledge of the physical properties that determine protein structure, such as the patterns of hydrophobic and hydrophilic residues in the sequence, salt bridges and hydrogen bonds, and secondary structural preferences of amino acids. Various approaches to apply these principles have been attempted. For example, the construction of α-helical and β-sheet proteins with native-like sequences was attempted by individually selecting the residue required at every position in the target fold (Hecht et al., Science 249:884–891 (1990); Quinn et al., Proc. Natl. Acad. Sci USA 91:8747–8751 (1994)). Alternatively, a minimalist approach was used to design helical proteins, where the simplest possible sequence believed to be consistent with the folded structure was generated (Regan et al., Science 241:976–978 (1988); DeGrado et al., Science 243:622–628 (1989); Handel et al., Science 261:879–885 (1993)), with varying degrees of success. An experimental method that relies on the hydrophobic and polar (HP) pattern of a sequence was developed where a library of sequences with the correct pattern for a four helix bundle was generated by random mutagenesis (Kamtekar et al., Science 262:16801685 (1993)). Among non de novo approaches, domains of naturally occurring proteins have been modified or coupled together to achieve a desired tertiary organization (Pessi et al., Nature 362:367–369 (1993); Pomerantz et al., Science 267:93–96 (1995)).

Though the correct secondary structure and overall tertiary organization seem to have been attained by several of the above techniques, many designed proteins appear to lack the structural specificity of native proteins. The complementary geometric arrangement of amino acids in the folded protein is the root of this specificity and is encoded in the sequence.

Several groups have applied and experimentally tested systematic, quantitative methods to protein design with the goal of developing general design algorithms (Hellingia et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. USA 92:8408–8412 (1995); Klemba et al., Nat. Struc. Biol. 2:368–373 (1995); Nautiyal et al., Biochemistry 34:11645–11651 (1995); Betzo et al., Biochemistry 35:6955–6962 (1996); Dahiyat et al., Protein Science 5:895–903 (1996); Dahiyat et al., Science 278:82–87 (1997); Dahiyat et al., J. Mol. Biol. 273:789–96; Dahiyat et al., Protein Sci. 6:1333–1337 (1997); Jones, Protein Science 3:567–574 (1994); Konoi, et al., Proteins: Structure, Function and Genetics 19:244–255 (1994)). These algorithms consider the spatial positioning and steric complementarity of side chains by explicitly modeling the atoms of sequences under consideration. In particular, WO98/47089, and U.S. Ser. No. 09/127,926 describe a system for protein design; both are expressly incorporated by reference.

A need still exists for a method of screening for cytokine mimetics. Thus, it is an object of the present invention to provide non-naturally occurring cell surface receptor analogs, capable of binding naturally occurring ligands, such as cytokines. It is a further aspect of this invention to provide nucleic acids encoding the receptor analogs and methods of using the receptor analogs for screening cytokine mimetics.

SUMMARY OF THE INVENTION

In accordance with the objects outlined above, the present invention provides non-naturally occurring cell surface receptor analogs, also termed "cell surface receptor analogs"

(e.g. the proteins are not found in nature) comprising amino acid sequences that are less than about 95–97% identical to the extracellular domains of corresponding naturally occurring cell surface receptors. The non-naturally occurring cell surface receptor analogs have at least one biological property of a naturally occurring cell surface receptor; for example, the non-naturally occurring cell surface receptor analog binds the natural ligand for the naturally occurring cell surface receptor. Thus, the invention provides non-naturally occurring cell surface receptor analogs with amino add sequences that have at least about 5% amino acid substitutions, deletions and/or insertions in their extracellular domain as compared to the naturally occurring cell surface receptor.

Further, the present invention provides non-naturally occurring ligands, also termed "ligand analogs" (e.g. the proteins are not found in nature) comprising amino acid sequences that are less than about 95–97% identical to corresponding naturally occurring ligands. The ligand analog have at least one biological property of a naturally occurring ligand; for example, the ligands and analog binds the natural receptor for the naturally occurring ligand. Thus, the invention provides ligand analogs with amino acid sequences that have at least about 5% amino acid substitutions, deletions and/or insertions when compared to the corresponding naturally occurring ligand.

In a further aspect, the present invention provides receptor analog conformers that have three dimensional backbone structures that substantially correspond to the three dimensional backbone structure of a naturally occurring cell surface receptor. The amino acid sequence of the conformer and the amino acid sequence of the naturally occurring cell surface receptor are less than about 95% identical with respect to the extracellular domain. In one aspect, at least about 90% of the non-identical amino acids are in a core region of the conformer. In other aspects, the conformer has at least about 100% of the non-identical amino acids in a core region.

In another aspect, the present invention provides receptor analog conformers that comprise a three dimensional backbone structure of an extracellular domain that substantially corresponds to the corresponding three dimensional backbone structure of a naturally occurring cell surface receptor complexed with its natural ligand. The amino acid sequence of the conformer and the amino acid sequence of the naturally occurring cell surface receptor, complexed with its natural ligand, are less than about 95% identical with respect to the extracellular domain. In one aspect, at least about 90% of the non-identical amino acids are in a core region of the conformer. In other aspects, the conformer has at least about 100% of the non-identical amino acids in a core region.

In a further aspect, the present invention provides ligand analog conformers that comprise a three dimensional backbone structure that substantially corresponds to the corresponding three dimensional backbone structure of a naturally occurring ligand. The amino acid sequence of the conformer and the amino acid sequence of the naturally occurring ligand, are less than about 95% identical. In one aspect, at least about 90% of the non-Identical amino acids are in a core region of the conformer. In other aspects, the conformer has at least about 100% of the non-identical amino acids in a core region.

In a further aspect, the invention provides recombinant nucleic acids encoding the non-naturally occurring cell surface receptor analogs, the ligand analogs, expression vectors comprising the recombinant nucleic acids, and host cells comprising either the recombinant nucleic acids or the recombinant nucleic acids and expression vectors.

In an additional aspect, the invention provides methods of producing the non-naturally occurring cell surface receptor analogs and the ligand analogs of the invention comprising culturing host cells comprising either the recombinant nucleic acids or the recombinant nucleic acids and expression vectors under conditions suitable for expression of the nucleic acids. The proteins may optionally be recovered.

In a further aspect, the invention provides for eukaryotic cells, prokaryotic cells, viruses and solid supports displaying a non-naturally occurring cell surface receptor analog.

In an additional aspect, the invention provides methods of screening for ligand analogs comprising the step of adding a candidate ligand to a non-naturally occurring cell surface receptor analog of the invention and determine the binding of said candidate ligand to said receptor analog.

In an additional aspect, the invention provides methods of screening for ligand analogs comprising the step of adding a candidate ligand to a non-naturally occurring cell surface receptor analog of the invention and determine the signaling activity of said receptor analog.

In a further aspect, the invention provides methods of screening for bioactive agents modulating the binding of a ligand analog to a receptor analog comprising the steps of (i) adding a ligand analog to a non-naturally occurring cell surface receptor analog, (ii) adding a candidate bioactive agent and (iii) determine whether said candidate bioactive agent modulates the binding of said ligand analog and said non-naturally occurring cell surface receptor analog.

In a further aspect, the invention provides methods of screening for bioactive agents modulating the binding of a ligand analog to a receptor analog comprising the steps of (i) adding a ligand analog to a non-naturally occurring cell surface receptor analog, (ii) adding a candidate bioactive agent and (iii) determine whether said candidate bioactive agent modulates the signaling activity of said non-naturally occurring cell surface receptor analog.

BRIEF DESCRIPTION OF THE DRAWINGS

FIGS. 8A, 8B, 8C, and 8D (SEQ ID NOS: 1–29) illustrate the sequence of EPOR the residues targeted by PDA design. The amino acid sequence shown in the query (SEQ ID NO: 1) corresponds to the extracellular domain of human EPOR. The signal sequence of the EPOR precursor (amino add residues 1–24 In GenBank accession #P19235) has been taken off. Thus, the 225 amino acid sequence shown corresponds to amino acid residues 25–249 of GenBank accession #P19235. The amino acid sequence shown in the subject (SEQ ID NO: 2) corresponds to the sequence used in the PDA design an differs from the query by not including amino acid residues 1–9 and 221–225 of the query (SEQ ID NO: 1). PDA sites and elbow_PDA sites, indicated by asterisks, refer to the sites used in the PDA design. The design was done first on domains D1 and D2 and the sequences were generated using d1 and d2 alone or in combination d 12. EPOR-PDA sequences are based on the structures of (i) the EPOR with an EPO mimetic peptide at 2.8 A resolution: 1ebp, (EPOR+EMP1)$_2$ dimer complex; (2) the EPOR with EPO at 2.8 A resolution: 1blw (also called 1cn4); and (3)EPOR with EPOR at 1.9 A resolution: 1eer. d1__211 or d2__211 means PDA on the left arm of EPOR dimer (amino acid residues 1–211); d1__422 or d2__422 means PDA on the right arm of EPOR dimer (amino acid residues 212–422); d1 and d2 without appendix mean PDA on EPOR dimer, ew refers to PDA on EPOR diner: ew1 refers to PDA on the left arm (1–211): ew2 refers to PDA on the right arm (212–422).

DETAILED DESCRIPTION OF THE INVENTION

Figure 1:
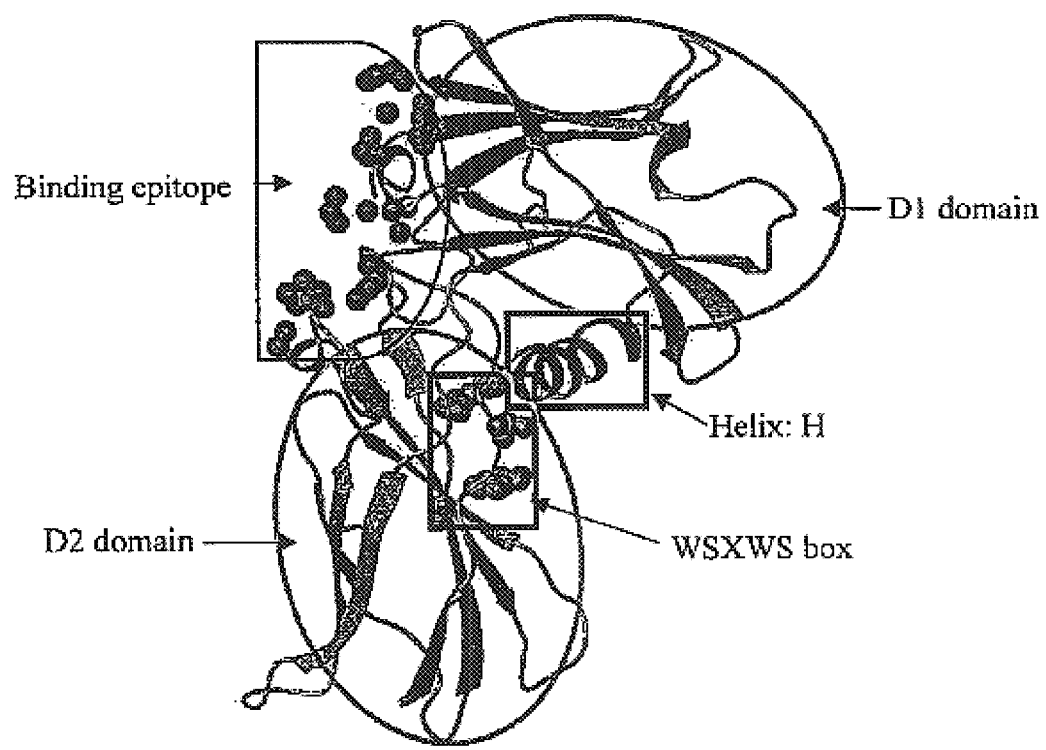
FIG. 1 illustrates the structure of one erythropoietin receptor (EPOR) monomer in the EPO-EPOR$_2$ complex. The side chains within 4.5 Å of EPO are shown as spheres in the binding epitope region, and the highly conserved residues are shown in the WSXWS box. The D1 and D2 domains are indicated by the oval regions and the N-terminal helix is indicated by *Helix*: H.

The present invention is generally directed to novel methods of screening for ligand analogs. Briefly, the invention may be described as follows. A receptor/ligand pair is chosen, and the receptor is modeled in an active conformation. The receptor analogs, provided herein, are stable receptor complexes held in a biologically active conformation similar to the structure of the corresponding naturally occurring receptors complexed with their cognate ligands. Creating such a structural mimic of an active, naturally occurring receptor combines the benefits of simple affinity-based screening with those of accurate but more complicated cell-based activity screening into a simple screening technique. Thus, as detailed further below, the receptor analogs of the invention may be used for high throughput screening.

Accordingly, the present invention provides non-naturally occurring cell surface receptor analogs.

By "non-naturally occurring" or "synthetic" herein is meant an amino acid sequence or a nucleotide sequence that is not found in nature; that is, an amino acid sequence or a nucleotide sequence that has been intentionally modified by man in the laboratory. Accordingly, by "naturally occurring" or "wild type" or grammatical equivalents, herein is meant an amino acid sequence or a nucleotide sequence that is found in nature and includes allelic variations; that is, an amino acid sequence or a nucleotide sequence that has not been intentionally modified by man in the laboratory.

By "cell surface receptor", "cell membrane receptor", "receptor" or grammatical equivalents herein is meant a proteinaceous molecule that has an affinity for a ligand. Included within this definition are proteinaceous molecules that are capable of being displayed on the surface of a cell, membrane or virus. In general, cell surface receptors have three components: an extracellular domain, which binds, as outlined above, the ligand, a transmembrane domain, to anchor the receptor, and an intracellular domain that usually is involved in signaling. Receptors may be exposed to the intracellular compartment (e.g., when located on cellular membranes, such as nuclear membranes, endoplasmatic reticulum membranes, mitochondrial membranes, etc.) or to the extracellular environment (e.g., when located on the surface of a cell or on the surface of a virus).

Receptors appear to fall into two general classes: type 1 and type 2 receptors. Type 1 receptors have generally two identical subunits associated together, either covalently or otherwise. They are essentially preformed dimers, even in the absence of ligand. The type 1 receptors include the insulin receptor and the IGF (insulin like growth factor) receptor. The type-2 receptors, however, generally are in a monomeric form, and rely on binding of one ligand to each of two or more monomers, resulting in receptor oligomerization and receptor activation. Type-2 receptors include the growth hormone receptor, the leptin receptor, the LDL (low density lipoprotein) receptor, the GCSF (granulocyte colony simulating factor) receptor, the interleukin receptors including IL-1, IL-2, IL-3, IL4, IL-5, ILL, IL-7, IL-8, IL-9, IL-11, IL-12, IL-13, IL-15, IL-17, etc., receptors, EGF (epidermal growth factor) receptor, EPO (erythropoietin) receptor, TPO (thrombopoietin) receptor, VEGF (vascular endothelial growth factor) receptor, PDGF (platelet derived growth factor; A chain and B chain) receptor, FGF (basic fibroblast growth factor) receptor, T-cell receptor, transferrin receptor, prolactin receptor, CNF (ciliary neurotrophic factor) receptor, TNF (tumor necrosis factor) receptor, Fas receptor, NGF (nerve growth factor) receptor, GM-CSF (granulocyte/macrophage colony stimulating factor) receptor, HGF (hepatocyte growth factor) receptor, LIF (leukemia inhibitory factor), TGFα/β (transforming growth factor α/β) receptor, MCP (monocyte chemoattractant protein) receptor and interferon receptors (α, β and γ). Further included are T cell receptors, MHC (major histocompatibility antigen) class I and class II receptors and receptors to the naturally occurring ligands, listed below.

Accession numbers for naturally occurring cell surface receptors are readily available. For example, amino acid sequences for the human erythropoietin receptor (EPOR) are available under P19235 and ZUHUR. Nucleotide sequences encoding human EPOR are available under NM_000121, M60459, and M34986. Amino acid sequences for the human tumor necrosis factor receptor (TNFR) are available under AAA36753, AAA36754, and AAA36756. Nucleotide sequences encoding human TNFR are available under M60275, M63121, and M58286. Amino acid sequences for the human growth hormone receptor (GHR) are available under AAA52555 and AAC50653. Nucleotide sequences encoding human GHR are available under AH002706 and U60179.

The invention provides non-naturally occurring cell surface receptor analogs. By "non-naturally occurring cell surface receptor analog", or "cell surface receptor analogs" or "receptor analog", or grammatical equivalents thereof, herein is meant a cell surface receptor having an amino acid sequence or a nucleotide sequence that is not naturally occurring. The receptor analogs and nucleic acids of the invention are distinguishable from naturally occurring cell surface receptors. Accordingly, by "naturally occurring cell surface receptor", or "wild type receptor", or grammatical equivalents thereof, herein is meant a cell surface receptor having an amino acid sequence or a nucleotide sequence that is naturally occurring.

In a preferred embodiment, the receptor analogs are naturally occurring human receptor conformers. By "conformer" herein is meant a protein that has a protein backbone 3D structure that is virtually the same but has significant differences in the amino acid side chains. That is, e.g., the receptor analogs of the invention define a conformer set, wherein all of the extracellular domains of the receptor analogs share a backbone structure and yet have sequences that differ by at least 3% when compared to the corresponding sequence of the naturally occurring human cell surface receptor. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the naturally occurring human cell surface receptor structure, with no more than 1.5 Å being preferred, and no more than 1 Å being particularly preferred. In general, these distances may be determined in two ways. In one embodiment, each potential conformer is crystallized and its three dimensional structure determined. Alternatively, as outlined below, the sequence of each potential conformer is run in the PDA program to determine whether it is a conformer.

In a preferred embodiment, the extracellular domain of a receptor analog has an amino acid sequence that differs from the sequence of a corresponding naturally occurring receptor by at least 3% of the residues. That is, the extracellular domains of receptor analogs of the invention are less than about 97% identical to the corresponding amino acid sequences of naturally occurring cell surface receptors. Accordingly, a receptor analog comprises an extracellular domain that is preferably less than about 97%, more preferably less than about 95%, even more preferably less than about 90% and most preferably less than 85% identical to the corresponding amino acid sequence of a naturally occurring cell surface receptor. In some embodiments the homology will be as low as about 75 to 80%. For example, based on the sequence corresponding to the potential extracellular domain of the human erythropoietin receptor, comprising amino acids 25–250 (accession number #P19235), a receptor analog has at least about 6–7 residues that differ from the naturally occurring receptor sequence (3%), with receptor analogs having from 11 different residues (about 5%) to upwards of 34 different residues (about 15%) being preferred. In some instances, the extracellular domains of receptor analogs have 3 or 4 different residues when compared to the corresponding naturally occurring human cell surface receptor sequence. Preferred receptor analogs have 1024 different residues with from about 10 to about 14 being particularly preferred (that is, 4–7% of the extracellular domain is not identical to that of a naturally occurring human cell surface receptor).

In a preferred embodiment, the receptor analog comprises amino acid substitutions within the extracellular domain(s), intracellular domain(s) and/or transmembrane region(s) when compared to the corresponding sequence of a naturally occurring cell surface receptor. In this embodiment one or more amino acids within one or more domains of the naturally occurring cell surface receptor are substituted by one or more amino acids to generate the receptor analog.

In another preferred embodiment, the receptor analog comprises amino acid insertions within the extracellular domain(s), intracellular domain(s) and/or transmembrane region(s) when compared to the corresponding sequence of a naturally occurring cell surface receptor. In this embodiment one or more amino acids within one or more domains of the naturally occurring cell surface receptor are inserted to generate the receptor analog. Insertions usually are on the order of from about 1 to 20 amino acids, although considerably larger insertions may be tolerated.

In another preferred embodiment, the receptor analog comprises amino acid deletions within the extracellular domain(s), intracellular domain(s) and/or transmembrane region(s) when compared to the corresponding sequence of a naturally occurring cell surface receptor. In this embodiment one or more amino acids within one or more domains of the naturally occurring cell surface receptor are deleted to generate the receptor analog. Deletions usually range from about 1 to 20 amino acids, although in some cases considerably larger deletions may be tolerated.

In a preferred embodiment, the receptor analog comprises a portion of the extracellular domain of a naturally occurring cell surface receptor. The term "portion", as used herein, with regard to a protein refers to a fragment of that protein. This fragment may range in size from 10 amino acid residues to the entire amino acid sequence minus one amino add.

The receptor analogs of the invention are distinguishable from naturally occurring cell surface receptors, however, they exhibit at least one biological function of a naturally occurring cell surface receptor. By biological function or biological property of a receptor analog or grammatical equivalents thereof, herein is meant any one of the properties or functions of a naturally occurring cell surface receptor, including, but not limited to: (1) ability to bind a ligand (which may be a naturally occurring ligand or a ligand analog, as further defined below); (2) ability to be displayed on the surface of a cell or on the surface of a virus; (3) ability to oligomerize; (4) ability to signal. In addition, depending on the biological role of the ligand, additional biological functions may be present, including, but not limited to (1) upon ligand binding, the ability to stimulate cell proliferation, particularly of hematopoietic stem cells; (2) upon ligand binding, the ability to inhibit cell proliferation, particularly of cancerous cells; (3) upon ligand binding, the ability to induce apoptosis, particularly of cancerous cells; and (4) upon ligand binding, the ability to treat disease.

Included within the definition of a receptor analog is a hybrid cell surface receptor analog. By "hybrid cell surface receptor analog" or "hybrid receptor analog" or grammatical equivalents herein is meant a receptor analog comprising individual domains derived from more than one naturally occurring cell surface receptor.

Thus, in a preferred embodiment, a hybrid receptor analog of the invention comprises (i) an extracellular domain similar to that of a first naturally occurring cell surface receptor, as described herein, and (ii) an intracellular domain(s) and/or transmembrane region that is/are similar to a domain found in a second and/or third naturally occurring cell surface receptor. For example, a receptor analog of the instant invention may comprise (i) the extracellular domain of an erythropoietin receptor, (ii) the transmembrane region of a thrombopoietin receptor and (iii) the intracellular domain of a granulocyte colony stimulating factor receptor. Another example includes a receptor analog, comprising (I) the extracellular domain and transmembrane domain of an erythropoietin receptor and (ii) the intracellular domain of a granulocyte colony stimulating factor receptor. Numerous combinations of these individual domains are within the scope of this invention.

Also included within the definition of receptor analogs are chimeric single chain receptor analogs. As outlined above, type-2 receptors are in a monomeric form, and generally rely on the binding of a ligand to the respective monomers to form an active receptor complex that is capable of signaling. As known in the art, these activated receptor complexes generally comprise identical monomeric subunits, comprising identical extracellular domains, identical transmembrane domains and identical intracellular (cytoplasmic) domains. In this embodiment of the invention, the receptor analog comprises a three dimensional extracellular structure resembling the three dimensional structure of an activated receptor complex comprising at least two monomers. However, the receptor analog comprises only one single amino acid chain with the capability to display the similar active extracellular domain as a naturally occurring receptor. The receptor analog, described in this embodiment, is referred to as "chimeric single chain receptor analog". Accordingly, such a chimeric single chain receptor analog is encoded by single gene.

A chimeric single chain receptor analog mimics an active receptor complex. In a preferred embodiment, and as further outlined below, such a chimeric single chain receptor analog is used to screen for candidate bioactive agents capable of binding to it. In one preferred embodiment, screening for a candidate bioactive agent is performed without the addition of a naturally occurring ligand or ligand analog.

Also included within the definition of receptor analogs are chimeric cell surface receptor complexes. By "chimeric cell surface receptor complex" or grammatical equivalents, herein is meant a receptor complex, comprising at least two receptor analog monomers, wherein each receptor analog monomer comprises a different amino acid sequence and wherein each monomer sequence is derived from the same corresponding naturally occurring cell surface receptor. For example, one receptor analog monomer is derived from the human EPO receptor and comprises, with respect to the naturally occurring sequence, amino acid exchanges in the extracellular domain, e.g., within positions 25–120. The second receptor analog monomer is also derived from the human EPO receptor, however, comprises amino acid exchanges within positions 121–250. In the above example, both receptor analog monomers are derived from the same naturally occurring cell surface receptor, comprise different extracellular domain sequences and identical transmembrane and intracellular domain regions. Generally, in this embodiment, at least two receptor analog monomers, generated as described herein, comprise a three dimensional extracellular structure resembling the three dimensional structure of an activated receptor complex. However, in contrast to a naturally occurring activated receptor complex, which comprises at least two identical naturally occurring receptor monomers, the chimeric cell surface receptor complex of the invention comprises at least two different receptor analog monomers. Each individual receptor analog monomer, herein designated as monomer "A" and monomer "B". Is designed to comprise an optimized amino acid sequences, allowing each monomer to specifically interact with another monomer. Based on the interaction between monomer "A" and monomer "B" a three dimensional structure is obtained, which resembles that of a corresponding naturally occurring activated cell surface receptor complex. In some embodiments, for example for trimeric receptors, such as TNFR, an optional monomer ECU may be included. By optimized amino acid sequence herein is meant an amino acid sequence that best fins, for example, the mathematical equation of the computational PDA process.

In one aspect of the above embodiment, receptor analog monomers "A" and "B" are designed that they do not strongly form oligomers with the same monomer, i.e. monomer "A" does not strongly multimerize to form an oligomeric "A" complex. Instead, as a consequence of the respective amino acid side chain exchanges, receptor analog monomer "A" preferably oligomerizes with receptor analog monomer "B" and vice versa in another aspect of this embodiment, a receptor analog monomer is designed to strongly interact with a naturally occurring cell surface receptor monomer to form a chimeric complex, resembling the three dimensional structure of naturally activated receptor complex. As such, the receptor analog monomer competes with the naturally occurring cell surface receptor dimerization. Accordingly, as will be appreciated by those in the art, in order to express the chimeric cell surface receptor complexes of the invention, usually at least two genes, one encoding monomer "A", and the second gene encoding monomer "B", are expressed in a host cell. Optionally a third gene, encoding monomer "C" or a naturally occurring cell surface receptor is also expressed in the same cell or within the same virus. However, as is known in the art, expression of polycistronic genes and/or polycistronic mRNAs is an option to simultaneously express more than one protein in the same cell or within the same virus.

As described above, the receptor analog of the invention have the capability to bind a ligand. By "ligand" herein is meant a molecule capable of binding to a receptor.

Upon binding of a ligand, a receptor may undergo a process called receptor activation. By "receptor activation" or grammatical equivalents herein is meant the biological function associated with ligand binding to a receptor. As will be appreciated by those in the ar, this will vary widely depending on the identity of the ligand and receptor. For example, as a result of ligand binding, cell surface receptors undergo conformational changes or multimerize into oligomeric receptor complexes or both. As a consequence of these events receptors become phosphorylated, or associate with a cellular protein, which then results in phosphorylation of either the receptor, the cellular protein, or yet another molecule. In this way signaling is accomplished.

In one aspect of the invention, a ligand capable of binding to a receptor analog, is a naturally occurring ligand. By "naturally occurring ligand" or "wild type ligand" or grammatical equivalents, herein is meant a ligand that is naturally occurring.

Naturally occurring ligands include but are not limited to, those with known structures (including variants), including cytokines IL-1ra, IL-1, IL-1a, IL-1b, IL-2, IL-3, IL-4, IL-5, IL-6, IL-8, IL-10, IFN-β, INF-γ, IFN-α-2a; IFN-α-2B, TNF-α; CD40 ligand (chk), human obesity protein leptin, GCSF, BMP-7, CNF, GM-CSF, MCP-1, macrophage migration inhibitory factor, human glycosylation-inhibiting factor, human rantes, human macrophage inflammatory protein II, hGH, LIF, human melanoma growth stimulatory activity, neutrophil activating peptide-2, CC-chemokine MCP-3, platelet factor M2, neutrophil activating peptide 2, eotaxin, stromal cell-derived factor-1, insulin, IGF-1, IGF-11, TGF-β1, TGF-β2, TGF-β3, TGF-α, VEGF, acidic-FGF, basic-FGF, EGF, NGF, BDNF (brain derived neurotrophic factor), CNF, PDGF, HGF, GCDNF (glial cell-derived neurotrophic factor), EPO, other extracellular signaling moieties. Including, but not limited to, hedgehog Sonic, hedgehog Desert, hedgehog Indian, hCG; coagulation factors including, put not limited to, TPA and Factor VIIa.

Accession numbers for naturally occurring ligands are readily available from NCBI, as described above. For example, amino acid sequences for the human erythropoietin are available under NP_000790, AAF23134 and AAF23132. Nucleotide sequences encoding human erythropoietin are available under AH009005, AH009003, and M11319. Amino acid sequences for the human tumor necrosis factor and human tumor necrosis factor beta (lymphotoxin) are available under AAD18091, and BAA02139, respectively. Nucleotide sequences encoding human tumor necrosis factor and human tumor necrosis factor beta (lymphotoxin) are available under AF129756 and D12614, respectively. Amino acid sequences for the human growth hormone are available under NP_000506, AAC42099 and CAA00065. Nucleotide sequences encoding human growth hormone are available under NM_000515, M36282 and AA00469.

In another embodiment, the ligand of the instant invention is a non-naturally occurring ligand that is distinguishable from a naturally occurring ligand. Accordingly, by "non-naturally occurring ligand" or "ligand analog" or grammatical equivalents thereof, herein is meant a ligand that is not naturally occurring.

In one preferred embodiment, the ligand analogs of the invention define a conformer set, wherein all of the domains of the ligand analog share a backbone structure and yet have sequences that differ by at least 3% when compared to the corresponding sequence of the naturally occurring ligands. That is, 350 the ligand analogs of the invention are less than about 97% identical to the corresponding amino acid sequences of naturally occurring ligands. Accordingly, a ligand analog comprises an amino acid sequence that is preferably less than about 97%, more preferably less than about 95%, even more preferably less than about 90% and most preferably less than 85% identical to the corresponding amino acid sequence of a naturally occurring ligand. In some embodiments the homology will be as low as about 75 to 80%. For example, a ligand analog, comprising 225 amino has at least about 6–7 residues that differ from the naturally occurring ligand (3%), with ligand analogs having from 11 different residues (about 5%) to upwards of 34 different residues (about 15%) being preferred. In some instances, the domains of ligand analogs have 3 or 4 different residues when compared to the corresponding naturally occurring human ligand sequence. Preferred ligand analogs have 10–24 different residues with from about 10 to about 14 being particularly preferred (that is, 4–7% of the amino acid sequence is not identical to that of a naturally occurring human ligand).

A ligand analog of the invention exhibits at least one biological function of a naturally occurring ligand.

By "biological function of a ligand analog" or "biological property of a ligand analog" or grammatical equivalents thereof, herein is meant any one of the properties or functions of a naturally occurring ligand, including, but not limited to: (1) ability to bind a naturally occurring receptor, (2) ability to bind a receptor analog; (3) ability to be secreted from a cell or a virus; (4) ability to oligomerize. In addition, depending on the biological role of the ligand, additional biological functions may be present. Including, but not limited to (1) the ability to stimulate cell proliferation after binding to a receptor, particularly of hematopoietic stem cells; (2) the ability to inhibit cell proliferation after binding to a receptor, particularly of cancerous cells; (3) the ability to induce apoptosis after binding to a receptor, particularly of cancerous cells; and (4) the ability to treat disease.

The cell surface receptors and the ligands may be from any number of organisms, with cell surface receptors and ligands from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (this is sometimes referred to herein as naturally occurring human cell surface receptor). As will be appreciated by those in the art, receptor analogs based on naturally occurring cell surface receptors and ligand analogs based on naturally occurring ligands from mammals other than humans may find use in animal models of human disease. As will be further appreciated by those in the art, a human cell surface receptor may bind a ligand from mammals other than humans.

The receptor analogs of the invention are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures, generally depending on the method of synthesis. Thus "amino add", or "peptide residue", as used herein means both naturally occurring and synthetic amino acids. For example, homo phenylalanine, citrulline and noreleucine are considered amino acids for the purposes of the invention. "Amino acid" also includes imino acid residues such as praline and hydroxyproline. The side chains may be in either the (R) or the (S) configuration. In the preferred embodiment, the amino acids are in the (S) or L-configuration. Stereoisomers of the twenty conventional amino acids, unnatural amino acids such as α,α-disubstituted amino acids, N-alkyl amino acids, lactic acid, and other unconventional amino acids may also be suitable components for proteins of the present invention. Examples of unconventional amino adds include, but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids. If non-naturally occurring side chains are used, non-amino acid substituents may be used, for example to prevent or retard in vivo degradations. Proteins including non-naturally occuring amino acids may be synthesized or in some cases, made recombinantly; see van Hest et al., FEBS Lett 428:(1–2) 68–70 May 22, 1998 and Tang et al., Abstr. Pap Am. Chem. S218:U138—U138 Part 2 Aug. 22, 1999, both of which are expressly incorporated by reference herein.

In a preferred embodiment, the ligand analogs are proteins.

For the remainder of the description of this invention, if not explicitly otherwise noted, receptor analog(s) and ligand analog(s), are collectively referred to as "analog protein(s)." It should be further noted that unless otherwise stated, all positional numbering within the sequence of an analog protein is based on the sequence of the corresponding naturally occurring protein and in particular, to the human sequences. That is, as will be appreciated by those in the art, an alignment of the naturally occurring protein and the analog protein can be done using standard programs, as is outlined below, with the identification of "equivalent" or "homologous" positions between the two proteins.

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol.

Biol., 215, 403–410, (1990) and Karlin et al., Proc. Natl. Acad. Sci. U.S.A., 90:5873–5787 (1993). A particularly useful BLAST program is the WU-BLAST-2 program which was obtained from Altschul et al., Methods in Enzymology, 266:460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to –22 bits. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the analog proteins identified herein is defined as the percentage of nucleotide residues in a candidate sequence that are identical with the nucleotide residues in the corresponding nucleotide sequence encoding the naturally occurring protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences encoding analog proteins, which contain either more or fewer amino acids than the corresponding naturally occurring proteins, it is understood that in one embodiment, the percentage of sequence identity is determined based on the number of identical amino acids in relation to the total number of amino acids. Thus, for example, sequence identify of sequences shorter than the sequence encoding the naturally occurring protein, is determined using the number of amino acids in the shorter sequence. In one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, analog proteins of the present invention may be shorter or longer than the amino acid sequences of the corresponding naturally occurring cell surface receptors. Thus, in a preferred embodiment, included within the definition of analog proteins are portions or fragments thereof. Fragments of analog proteins are considered receptor analogs or ligand analogs if a) they share at least one antigenic epitope; b) have at least the indicated homology; c) and preferably have biological activity as defined herein.

As is more fully outlined herein, any of the receptor analog variations may be combined in any way to form additional novel receptor analogs, novel chimeric cell surface receptor complexes and novel hybrid cell surface receptor analogs comprising at least two different receptor analogs.

In addition, analog proteins can be made that, for example, comprising epitope or purification tag, or other fusion sequences, etc., as outlined below. For example, the analog proteins of the invention may be fused to other therapeutic proteins such as IL-11 or to other proteins such as Fc or serum albumin for pharmacokinetic purposes. See for example U.S. Pat. Nos. 5,766,883 and 5,876,969, both of which are expressly incorporated by reference.

Analog proteins may also be identified as being encoded by analog protein (AP) nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, an AP nucleic acid encodes an analog protein. As will be appreciated by those in the art, due to the degeneracy of the genetic code, an extremely large number of nucleic acids may be made, all of which encode the analog proteins of the present invention. Thus, having identified a particular amino acid sequence, those skilled in the art could make any number of different nucleic acids, by simply modifying the sequence of one or more codons in a way which does not change the amino acid sequence of the analog protein.

In one embodiment, the nucleic acid homology is determined through hybridization studies. Thus, for example, nucleic acids which hybridize under high stringency to a nucleic acid encoding a naturally occurring protein or its complement and encode an analog protein is considered an analog protein gene.

High stringency conditions are known in the art; see for example Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions, e.g. are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment less stringent hybridization conditions are used; for example, moderate or low stringency conditions may be used, as are known in the art; see Sambrook, supra, Ausubel, supra, and Tijssen, supra.

The analog proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated AP nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism it will replicate non recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is nominally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an analog protein from one organism in a different organism or host cell. Alternatively, the protein may be made at a significantly higher concentration than is normally seen, through the use of a inducible promoter or high expression promoter, such that the protein is made at increased concentration levels. Furthermore, all of the analog proteins outlined herein are in a form not normally found in nature, as they contain amino acid substitutions, insertions and deletions, with substitutions being preferred, as discussed below.

Also included within the definition of analog proteins of the present invention are amino acid sequence variants of the analog protein sequences outlined herein. That is, an analog protein may contain additional variable positions as compared to a starting analog protein. These variants fall into one or more of three classes: substitutional, insertional or deletional variants. These variants ordinarily are prepared by site specific mutagenesis of nucleotides in the DNA encoding an analog protein, using cassette or PCR mutagenesis or other techniques well known in the art, to produce DNA encoding the variant, and thereafter expressing the DNA in recombinant cell culture as outlined above. However, variant analog protein fragments having up to about 100–150 residues may be prepared by in vitro synthesis using established techniques. Amino acid sequence variants are characterized by the predetermined nature of the variation, a feature that sets them apart from naturally occurring allelic or interspecies variations.

Directed molecular evolution can be used to create analog proteins with novel function and properties. There is a wide variety of methods known for generating and evaluating sequences. These include, but are not limited to, sequence profiling (Bowie and Eisenberg, Science 253:16470, (1991)), rotamer library selections (Dahiyat and Mayo, Protein Sci 5:895903 (1996); Dahiyat and Mayo, Science 278:82–7 (1997); Desjarlais and Handel, Protein Science 4:20062018 (1995); Harbury et al, Proc. Natl. Acad. Sci. U.S. 92:8408412 (1995); Kono et al., Proteins: Structure, Function and Genetics 19:244–255 (1994); Hellinga and Richards, Proc. Natl. Acad. Sci. U.S.A. 91:5803–5807 (1994)); and residue pair potentials (Jones, Protein Science 3:567–574, (1994)).

In a preferred embodiment, the analog proteins, are designed using a method termed "Protein Design Automation", or PDA, that utilizes a number of scoring functions to evaluate sequence stability. PDA was previously described in WO98/47089 and U.S. Ser. No. 09/127,926, both of which are expressly incorporated by reference in their entirety. PDA is a computational modeling system that allows the generation of extremely stable proteins without necessarily disturbing the biological functions of the protein itself. In this way, novel receptor analogs and ligand analogs and their nucleic acids are generated, that can have a plurality of mutations in comparison to their naturally occurring counterparts and yet retain significant activity.

The computational method used to generate and evaluate the analog proteins of the invention is briefly described as follows. In a preferred embodiment, the computational method used to generate the primary library is Protein Design Automation (PDA), as is described in U.S.S.N.s 60/061,097, 60/043,464, 60/054,678, 09/127,926 and PCT US98/07254, all of which are expressly incorporated herein by reference. Briefly, PDA, which can be applied to any protein, can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining side chains is called the template. Each variable residue position is then preferably classified as a core residue, a surface residue, or a boundary residue; each classification defines a subset of possible amino acid residues for the position (for example, core residues generally are selected from the set of hydrophobic residues, surface residues generally are selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include, but are not limited to, the energy of van der Waal's forces, the energy of hydrogen bonding, the energy of secondary structure propensity, the energy of surface area solvation and the electrostatics. Thus, the total energy of each rotamer interaction, both with the backbone and other rotamers. Is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to gene rate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. In addition, as will be appreciated by those in the art, a Monte Carlo search may be done from a DEE run that is not completed; that is, a partial DEE run that his a number of sequences may be used to generate a Monte Carlo list.

As outlined in U.S.S.N. 09/127,926, the protein backbone (comprising (for a naturally occurring protein) the nitrogen, the carbonyl carbon, the a-car bon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization (Mayo et al., J. Phys. Chem. 94:8897 (1990)) of atomic coordinate positions to minimize the Dreiding force field with no electrostatics. Generally from about 110 to about 250 steps is preferred, with about 50 being most preferred.

The protein backbone structure contains at least one variable residue position. As is known in the at, the residues, or amino acids, of proteins are generally sequentially numbered starting with the Na terminus of the protein. Thus a protein having a methionine at it's N-terminus is said to have a methionine at residue or amino acid position 1, with the next residues as 2, 3, 4, etc. At each position, the wild type (i.e. naturally occurring) protein may have one of at least 20 amino acids. In any number of rotamers. Each analog protein residue can differ from the naturally occurring protein at an equivalent position. This is called a variable residue position. By "variable residue position" herein is meant an amino acid position of the protein to be designed that is not fixed in the design method as a specific residue or rotamer, generally the wild-type or naturally occurring protein residue or rotamer.

In a preferred embodiment, all of the residue positions of the protein are variable. That is, every amino acid side chain may be altered in the methods of the present invention.

In an alternate preferred embodiment, only some of the residue positions of the protein are variable, and the remainder are "fixed", that is, they are identified in the three dimensional structure as being a particular amino acid in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the active site), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.90, of the total number of rid residues. Thus, for example, it may be possible to change only a few (or one) residues, or most of the residues, with all possibilities in between.

In a preferred embodiment, residues which can be fixed include, but are not limited to, structurally or biologically functional residues. For example, residues which are known to be important for biological activity, such as the residues which form the binding site for a binding partner (ligand/receptor, antigen antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable biological activity but with a preservation of binding, etc.

In a preferred embodiment, each variable position is classified as either a core, surface or boundary residue position, although in some cases, as explained below, the variable position may be set to glycine to minimize backbone strain.

In one embodiment, only core residues are variable residues; alternate embodiments utilize methods for designing analog proteins containing core, boundary and surface variable residues; core and surface variable residues: core and boundary variable residues; surface and boundary variable residues; as well as surface variable residues alone, or boundary variable residues alone. In general, preferred embodiments do not utilize surface variable residues, as this can lead to undesirable antigenicity; however, in applications that are not related to therapeutic use of the analog proteins, it may be desirable to after surface residues. Any combination of core, surface and boundary positions can be utilized.

The classification of residue positions as core, surface or boundary may be done in several ways, as will be appreciated by those in the art and outlined in WO98/47089, hereby incorporated by reference in its entirety. In a preferred embodiment, the classification is done via a visual scan of the original protein backbone structure. Including the side chains, and assigning a classification based on a subjective evaluation of one skilled in the art of protein modeling. Alternatively, a preferred embodiment utilizes an assessment of the orientation of the $C\alpha$–$C\beta$ vectors relative to a solvent accessible surface computed using only the template $C\alpha$ atoms. In a preferred embodiment, the solvent accessible surface for only the $C\alpha$ atoms of the target fold is generated using the Connolly algorithm with a probe radius ranging from about 4 to about 12 Å, with from about 6 to about 10 Å being preferred, and 8 Å being particularly preferred. The $C\alpha$ radius used ranges from about 1.6 Å to about 2.3 Å, with from about 1.8 to about 2.1 Å being preferred, and 1.95 Å being especially preferred. A residue is classified as a core position if a) the distance for its $C\alpha$, along its $C\alpha$–$C\beta$ vector, to the solvent accessible surface is greater than about 46 Å, with greater than about 5.0 Å being especially preferred, and b) the distance for its $C\beta$ to the nearest surface point is greater than about 1.5–3 Å, with greater than about 2.0 Å being especially preferred. The remaining residues are classified as surface positions if the sum of the distances from their $C\alpha$, along their $C\alpha$–$C\beta$ vector, to the solvent accessible surface, plus the distance from their $C\beta$ to the closest surface point was less than about 2.5–4 Å, with less than about 2.7 Å being especially preferred. All remaining residues are classified as boundary positions.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that is evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the $\alpha$ scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, iscleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino add; 2) the nitrogen atom of the current residue; 3) the α-carbon of the current residue; and 4) the carbonyl carbon of the current residue) greater than 0°., the position is set to glycine to minimize backbone strain.

Once the group of potential rotamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is usedin the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec}$$ Equation 1

In Equation 1, the total energy is the sum of the energy of the van der Waals potential ($E_{vdw}$), the energy of atomic salvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S.S.N.s 60/061,097, 60/043,464, 60/054, 678, 09/127,926 and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

Once the singles and doubles energies are calculated and stored, the next step of the computational processing may occur. As outlined in U.S. Ser. No. 09/127,926 and PCT US98/07254, preferred embodiments utilize a Dead End Elimination (DEE) step, and preferably a Monte Carlo step.

The computational processing results in a set or library of optimized protein sequences. These optimized protein sequences are generally, but not always, significantly different from the wild-type sequence from which the backbone was taken. That is, each optimized protein sequence preferably comprises at least about 310% variant amino acids from the starting or wild-type sequence, with at least about 10–15% being preferred, with at least about 15–20% changes being more preferred and at least about 30% changes being particularly preferred.

The cutoff for the optimized protein sequences is then enforced, resulting in a set of sequences forming a library of optimized protein sequences. As outlined above, this may be done in a variety of ways, including an arbitrary cutoff, an energy limitation, or when a certain number of residue positions have been varied. In general, the size of the library will vary with the size of the protein, the number of residues that are changing, the computational methods used, the cutoff applied and the discretion of the user. In general, it is preferable to have the library be large enough to randomly sample a reasonable sequence space to allow for robust screening. Thus, libraries that range from about 50 to about $10^{13}$ are preferred, with from about 1000 to about $10^7$ being particularly preferred, and from about 1000 to about 100,000 being especially preferred.

In a preferred embodiment, although this is not required, the library comprises the globally optimal sequence in its optimal conformation, i.e. the optimum rotamer at each variable position. That is, computational processing is run until the simulation program converges on a single sequence which is the global optimum. In a preferred embodiment, the library comprises at least two optimized protein sequences. Thus for example, the computational processing step may eliminate a number of disfavored combinations but be stopped prior to convergence, providing a library of sequences of which the global optimum is one. In addition, further computational analysis, for example using a different method, may be run on the library, to further eliminate sequences or rank them differently. Alternatively, as is more fully described in U.S.S.N.s 60/061,097, 60/043,464, 60/054,678, 09/127,926 and PCT US98/07254, the global optimum may be reached, and then further computational processing may occur, which generates additional optimized sequences in the neighborhood of the global optimum.

In addition, in some embodiments, library sequences that did not make the cutoff are included in the library. This may be desirable in some situations to evaluate the library generation method, to serve as controls or comparisons, or to sample additional sequence space. For example, in a preferred embodiment, the wild-type sequence is included.

The present invention utilizes a variety of methods to generate analog proteins, in particular receptor analogs, e.g., analogs with an "activated" conformation. In a preferred embodiment, the analog proteins of the invention are designed by Protein design Automation (PDA). Protein design using PDA utilizes a three dimensional structure of the target protein, e.g. a natural ligand or a natural receptor.

Evidence from structural and mutagenesis studies both indicate that x-ray crystal structures of e.g., cytokine receptors in complex with their natural cytokine ligands are indeed the optimal conformations for the receptor complexes.

Known protein structures can be obtained from the National Center for Biotechnology Information (NCBI) at e.g. www.ncbi.nlm.nih.gov/structure. The NCBI Structure Group maintains MMDB, a database of macromolecular 3D structures, as well as tools for their visualizaton and comparative analysis. MMDB, the Molecular Modeling Data Base, contains experimentally determined biopolymer structures obtained from the Protein data Bank (PDB). Thus, e.g., accession number 1 EER provides the crystal structure of human erythropoietin complexed to its receptor at 1.9 Angstroms; accession number 1CN4 provides erythropoietin complexed with the extracellular domains of the erythropoietin receptor; and accession numbers 1EBA and 1EBP provide the structures of complexes between the extracellular domain of the erythropoietin receptor an inactive peptide or agonist peptide, respectively.

Several regions can be designed in order to constrain and stabilize, e.g., a cytokine receptor complex in its optimal conformation without disrupting ligand binding: (1) the interface between the two monomers in the complex (inter-monomer interface); (2) the angle between different domains within a receptor monomer such as D1 and D2 (intra-monomer interface); (3) domain D1; (4) domain D2; (5) the conserved WSXWS (SEQ ID NO: 30) box; and (6) the N-terminal helix (see FIG. 1). The conformations of these regions vary significantly in the presence and absence of a ligand, agonist or antagonist. Owing to the character of the different cytokine receptor structures, the PDA strategy employed is dependent on the structure of the respective cytokine receptor.

In one embodiment, protein design is used to constrain the inter-monomer interface as well as the intra-monomer interface between domains D1 and D2. This "Type-I Design" is applicable to coupled receptors with direct inter-monomer contact of the respective extracellular domains (ECD), including, but not limited to those found in the human growth hormone receptor (hGHR) and the erythropoietin receptor (EPOR). Also, within this embodiment are coupled receptors that are constrained only in their inter-monomer interface and receptors that are constrained only in their intra-monomer interface between domains D1 and D2.

In a preferred embodiment the receptor analog is an erythropoietin receptor (EPOR) analog. Complex structure between EPO, EPO mimetics and EPOR have been published and coordinates have been released (e.g., 1eer; see above and FIG. 1). These structures and the currently available receptor dimer structure in complex with EMP1, a peptide agonist, shows that the two receptor monomers contact each other across a small inter-monomer interface. The contact residues are two arginine and one leucine residues (Arg155, L175 and R178) in 1ebp. In 1eer, the contact residues are Asp133 and Ser135. There are at least four targeting sites on EPOR for protein design: (1) the interface between two receptors, (2) the interface between domain D1 and D2, (3) domain D1, and (4) domain D2. These sites are distant from the ligand binding sites. The different design strategies that follow may be employed to stabilize the complete EPOR and/or the extracellular domain (ECD) of EPOR, comprising residues 1–225. The ECD is the fragment of EPOR solved in x-ray structure; it binds EPO with the same affinity as the intact EPOR.

In a preferred embodiment, protein design comprises the inter-monomer interface between EPO receptors. At least three contacting residues of each EPOR and nearby positions are designed to reconfigure the interface between the two receptors and engineer hydrogen bonds to fix the orientation between the receptors. In one aspect of this embodiment, the reconfiguration of the interface between receptors is done by introducing a disulfide linkage. In yet another aspect of this invention, reconfiguration of the interface between receptors is done using other known crosslinking agents as outlined below. The contact residues may vary depending on whether EPOR is bound by its naturally occurring ligands, EPO, or by an EPO mimetic.

Thus, conformational specific cross-linking is possible within different EPOR and EPOR analog complexes.

In one aspect of this embodiment, the receptor analog is designed based on the structure of EPOR complexed with an EPO mimetic peptide. Herein the three contact residues are Arg155, Leu175 and Arg178 (see 1ebp in FIG. 8).

In another aspect of this embodiment, the receptor analog is designed based on the structure of EPOR complexed with EPO. Herein the contact residues are Asp133, and Ser135 (see 1eer in FIG. 8).

In another preferred embodiment, protein design comprises the stabilization of domains D1 and D2, either alone or in combination. In one aspect of this embodiment, the amino acid residues chosen for design include, but are not limited to one or more of the following amino acid residues of EPOR within D1: Trp40, Tyr53, Phe55, Tyr57, Leu69, Val79, Phe81, Leu85, Leu96, Leu98, Val100, and Tyr109 or within D2: Leu127, Ala129, Val136, Leu140, Trp142, Tyr156, Val158, Val160, Ile174, Leu183, Tyr192, Phe194, Val196, Ala198, Gly207, and Leu218 (see FIG. 8). Positions are chosen that should either not contact the residues involved in ligand-receptor interaction or should not significantly reduce the ligand-receptor interaction.

In one aspect of this embodiment, protein design comprises stabilization of domain D1 alone. Positions are chosen that should either not contact the residues involved in ligand-receptor interaction or should not significantly reduce the ligand-receptor interaction. In one aspect of this embodiment, the contact residues include, but are not limited to one or more of the following amino acid residues of EPOR: Trp40, Tyr53, Phe55, Tyr57, Leu69, Val79, Phe81, Leu85, Leu96, Leu98, Val100, and Tyr109 (see FIG. 8).

In another aspect of this embodiment, protein design comprises stabilization of domain D2 alone. Positions are chosen that should either not contact the residues involved in ligand-receptor interaction or should not significantly reduce the ligand-receptor interaction. In one aspect of this embodiment, the contact residues include, but are not limited to one or more of the following amino acid residues of EPOR: Leu127, Ala129, Val138, Leu140, Trp142, Tyr156, Val158, Val160, Ile174, Leu183, Tyr192, Phe194, Val196, Ala198, Gly207, and Leu218 (see FIG. 8).

In another preferred embodiment, protein design comprises the conserved WSXWS (SEQ ID NO: 30) box. Positions are chosen that should either not contact the residues involved in ligand-receptor interaction or should not significantly reduce the ligand-receptor interaction. In one aspect of this embodiment, the contact residues include one or more of the following amino acid residues of EPOR: Trp209, Ser210, Ala211, Trp 212, and Ser213.

In another preferred embodiment, protein design comprises the stabilization of the N-terminal helix. Positions are chosen that should either not contact the residues involved in ligand-receptor interaction or should not significantly reduce the ligand-receptor interaction. In one aspect of this embodiment, the contact residues include, but are not limited to one or more of the following amino acid residues of EPOR: Phe11, Ala15, Leu17, Leu18, Ala19, Phe29, Val37, Phe39 (see FIG. 8).

In a preferred embodiment, positions designed comprising (1) the inter-monomer interface between EPO receptors; (2) the interface between domain D1 and D2, (3) domain D1; (5) domain D2; (6) the WSXWS (SEQ ID NO: 30) box and (4) the N-terminal helix are combined to give a combined protein design for both interfaces. Any combination of designed positions, either individually or in groups is within the scope of the invention.

In another preferred embodiment, disulfide bonds are designed to link the two receptor monomers at inter-monomer contact sites. In one aspect of this embodiment the two receptors are linked at distances <5 A. In another aspect of this embodiment, the linkage occurs between dimerization motifs, such as coiled coil, fused to the receptor analog. Suitable amino acid residues for linkage are Arg155, Leu175 and Arg178 (see 1ebp complex; FIG. 8) and Asp133 and Ser135 (see 1eer complex; FIG. 8).

In a preferred embodiment, a dimeric coiled-coil [designed by e.g., PDA to increase stability and specificity, e.g., see Dahiyat et al., Protein Science 6:1333–7 (1997)] is linked to the ECD of EPOR to assist dimer assembly; the linkage can be designed so that the angular register of the EPOR dimer favors the optimal conformation and the linker length and composition can be designed to complement the receptor structure. Coiled-coil motifs may be added to other receptor analogs and ligand analogs of the invention.

In a preferred embodiment, the coiled coil motif comprises, but is not limited to one of the following sequences: RMEKLEQKVKELLRKNERLEEEVERLKQLYGER, (SEQ ID NO: 31) based on the structure of GCN4 AMLESEVSALESEVASLESEVAAL, (SEQ ID NO: 32) and LAAVKSKLSAVKSKLASVKSKLAA, (SEQ ID NO: 33) coiled-coil leucine zipper regions defined previously (see Martin et al., EMBO J. 13(22):5303–5309 (1994), incorporated by reference). Other coiled coil sequences from e.g. leucine zipper containing proteins are known in the art and are used in this invention. See, for example, Myszka et al., Biochem. 33:2362–2373 (1994), hereby incorporated by reference).

In another preferred embodiment, the analog receptor includes a linker. For example, the coiled coil motif may be fused to a receptor analog via a linker. By "linker", "linker sequence", "spacer, tethering sequence" or grammatical equivalents thereof, herein is meant a molecule or group of molecules (such as a monomer or polymer) that connects two molecules and often serves to place the two molecules in a preferred configuration, e.g., so that a ligand can bind to a receptor with minimal steric hindrance. In one aspect of this embodiment, the linkers include glycine-serine polymers (including, for example, $(GS)_n$, $(GSGGS)_n$, (SEQ ID NO: 34) $(GGGGS)_n$, (SEQ ID NO: 35) and $(GGGS)_n$, (SEQ ID NO: 36) integer of at least one), glycine-alanine polymers, alanine-serine polymers, and other flexible liners such as the tether for the shaker potassium channel, and a large variety of other flexible linkers, as will be appreciated by those in the art Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Figure 2:
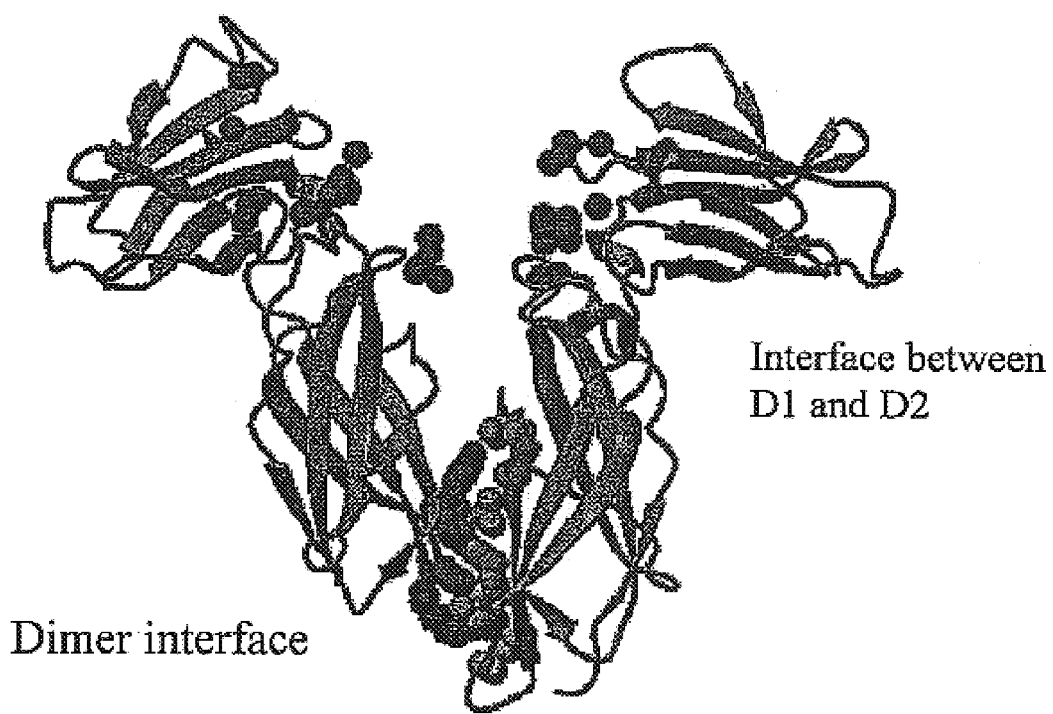
FIG. 2 illustrates the structure of the binding interface between human growth hormone receptor (hGHR) with its ligand (spheres in upper portion of Figure) within 5Å and the contact interface between the two receptor monomers (spheres in lower portion of Figure).

In another preferred embodiment, the analog receptor is a human growth hormone receptor (hGHR) analog. hGHR has a large interface buried between two receptors upon dimerization (FIG. 2). The interface is formed by the same residues of each receptor determined by the approximate 2-fold symmetry of the receptor in the complex. In this embodiment, the interface between these two receptors is designed generating a single sequence for the designed receptor analog. Further included within this embodiment are hGHR analogs comprising designed intra-monomer sites to stabilize the conformation of each monomer. The contact residues between ligand and receptors are far away from the inter-monomer contact sites between the two receptors and as such, binding of the ligand is not compromised.

Figure 4:
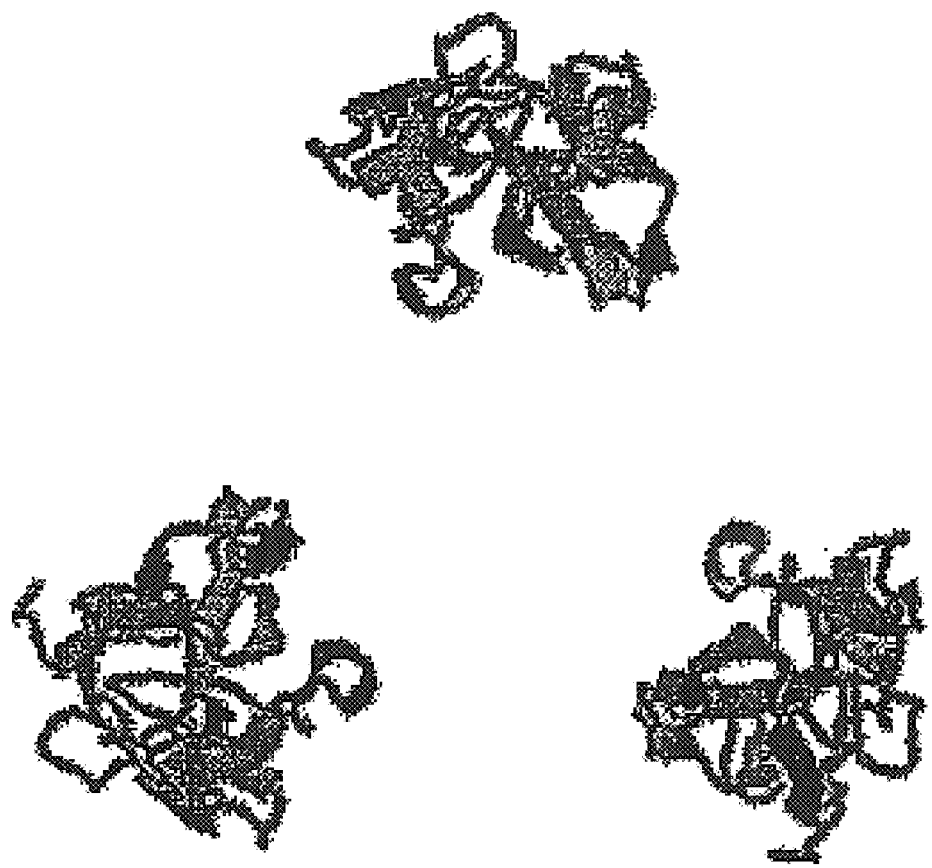
FIG. 4 illustrates the structure of the tumor necrosis factor receptor (TNFR) trimer.
Figure 5:
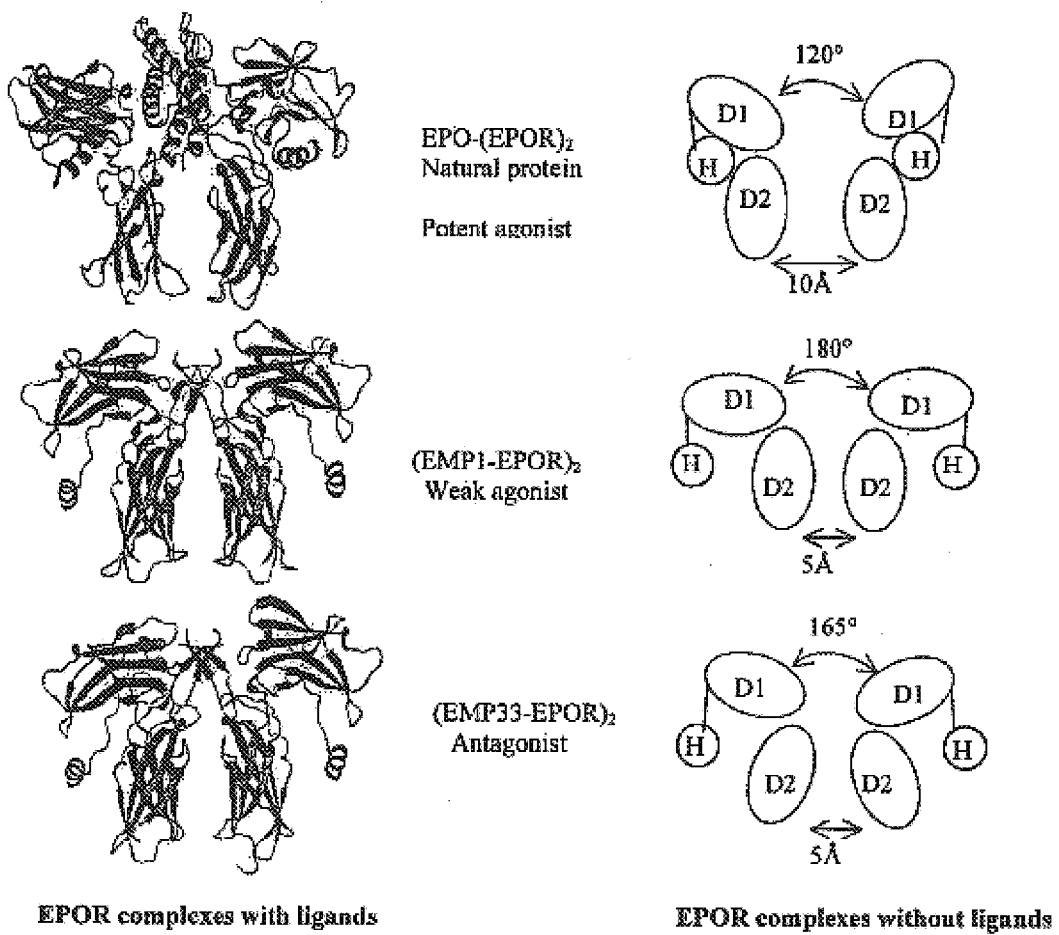
FIG. 5 illustrates on the left side x-ray structures of EPO receptors in complex with ligands, such as the naturally occurring erythropoietin: EPO-EPOR$_2$; EMP1, a weak agonist: (EMP1-EPOR); and EMP33, an antagonist: (EMP33-EPOR)$_2$. At the right, 2-dimensional schematic drawings of EPO receptors in complexes are shown (the ligands are not shown). Two 7-beta-strand domains, D1 and D2, and the N-terminal helix (H) are shown. The orientation (angle) between the two receptor monomers is different for each complex, and the separation between the two monomers and relative position of the α-helix in the EMP1 and EMP33 complexes differs from that of the EPO complex.

In another preferred embodiment, the receptor analog is a tumor necrosis factor receptor (TNFR) analog. For TNFR, there is little or no interference between receptors in the trimer structure (FIG. 4).

In uncoupled receptors that do not contact each other in the x-ray structure, including, but not limited to TNFR, the interface between D1 and D2 domains is stabilized, constraining each monomer in its active conformation. Thus, in this preferred embodiment, the interface between D1 and D2 is designed, e.g., by PDA to rigidity the orientation between them. Positions are chosen that either do not contact the residues involved in ligand-receptor interaction or do not have a negative effect on ligand-receptor interaction.

In a preferred embodiment, protein design is used to enhance the stability and specificity of protein oligomerization motifs, in particular, dimericirimeric coiled-coil proteins. These oligomerization motifs are used to assemble the receptor monomers into the functional active oligomerization state by fusing e.g. the PDA-designed motif to the receptor. A major goal is to stabilize the coiled-coil trimeric motif to maximize the oligomerization of TNFR and to prevent incorrect oligomerization, such as dimers and tetramers. Protein design such as PDA can be used for this purpose because a trimeric coiled-coil x-ray structure is available. Although this "Type-II Design" approach is not as direct as the "Type-1 Design" approach, the entropically constrained receptor complex is still far better suited for methods of screening for ligand analogs and bioactive agents.

In a preferred embodiment, this "Type-II Design" approach is used to introduce a coiled-coil trimerization domain fused to the TNFR. In one aspect of this embodiment, the coiled-coil trimerization domain is fused to the carboxy terminus of TNFR (see FIG. 7).

In another preferred embodiment, the coiled-coil (designed e.g., by PDA with the increased stability and specificity) is fused to the extracellular fragment of TNFR to assist the assembly of TNFR trimer, the linkage should be registered to favor the TNFR trimer in an optimal conformation. Positions are chosen that either do not contact the residues involved in ligand-receptor interaction or do not have a negative effect on ligand-receptor interaction.

Figure 6:
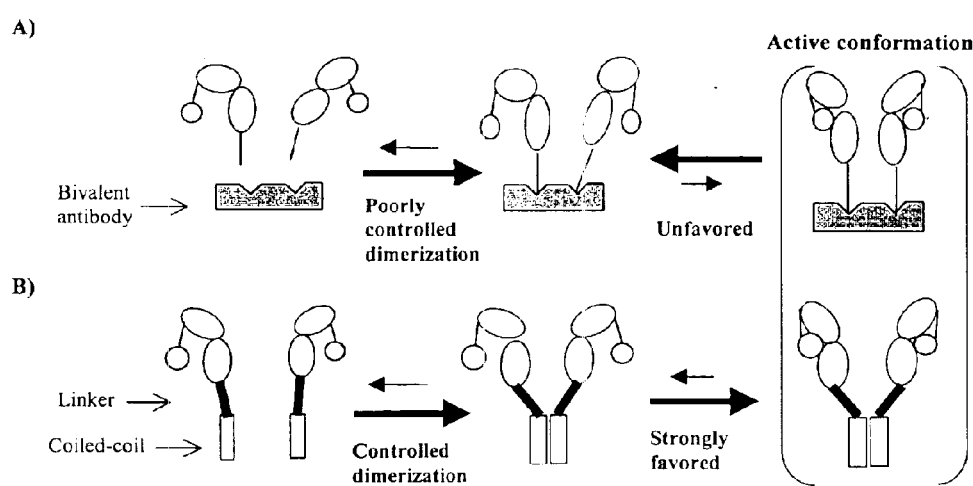
FIG. 6 illustrates in row A) an in vitro screen for EPO mimics using bivalent antibodies [Wrighton et al., Science 273:458–64 (1996)]. This approach suffers from poorly controlled EPOR dimerization; the bioactive dimer conformation (shown in brackets) is not favored (in equilibrium with large ensemble of inactive conformations. In row B), an approach using coiled coil fused to an EPOR is shown. Using a coiled coil approach with adjustable linker length between the coiled coil and e.g. the D2 domain of EPOR allows more control over dimerization and stabilization of dimer orientation. Using e.g., PDA design, the bioactive conformation will be strongly favored.
Figure 7:
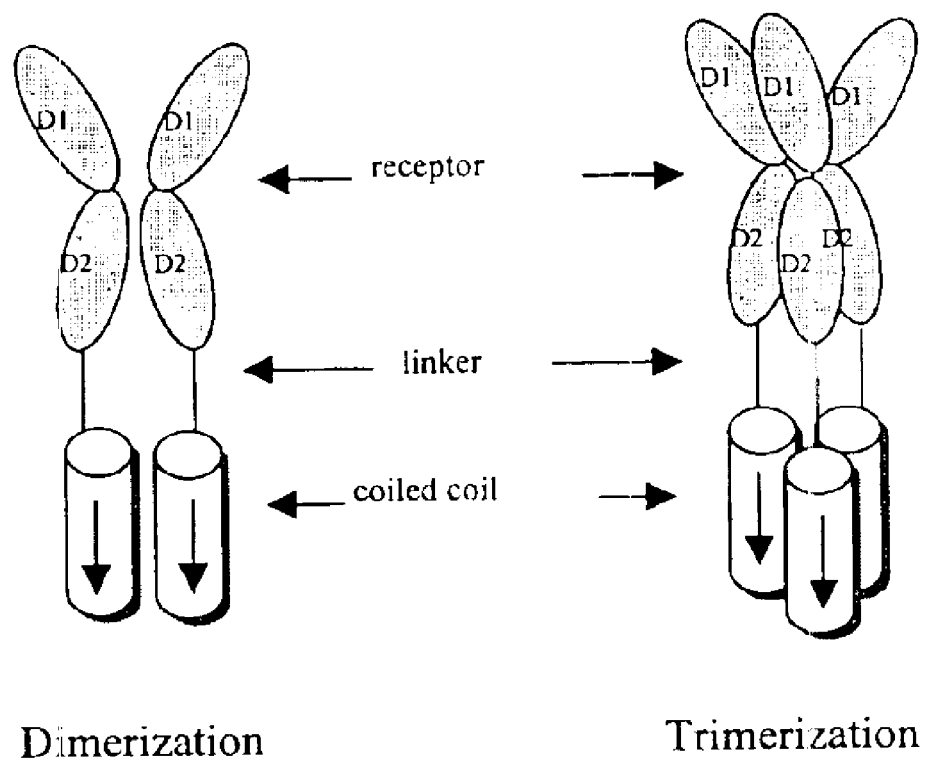
FIG. 7 illustrates schematically the coiled coil motif being fused to the D2 domain of a coupled receptor, such as EPOR, leading to dimerization and the coiled coil motif being fused to the D2 domain of an uncoupled receptor, such as TNFR, leading to trimerization.

In a further aspect of this embodiment, a linker sequence between receptor monomer and attachment point of the coiled coil is designed to control the relative spacing and orientation between them. The orientation and position of the linker segment between the oligomerization domain and the receptor are optimized to favor the desired receptor orientation (FIG. 6 and FIG. 7).

In another preferred embodiment, the receptor analog is a tumor necrosis factor receptor II (TNFR-II) receptor analog. In this embodiment, exemplified by TNFR-II, when no x-ray structure information for the respective receptor/ligand complex is available, the present invention provides a "Type-III Design" approach, wherein homology modeling performed by e.g., PDA in combination with oligomerization-assisted receptor assembly is used to design functional receptor complexes. This approach can be applied to design other cytokine receptors that share sequence homology with existing cytokine receptor x-ray structures.

In a preferred embodiment, modeling of the TNFR-II receptor (P75 kD) sequence is performed onto the TNFR-1 receptor (P55 kD) structure. TNFR-II receptor (P75 kD) belongs to the same class of receptor family as TNFR-I receptor (P55 kD).

In a preferred embodiment, this TNFR-II receptor model structure is used to guide mutagenesis experiments to identify ligand binding sites on the TNFR-II receptor.

Figure 3:
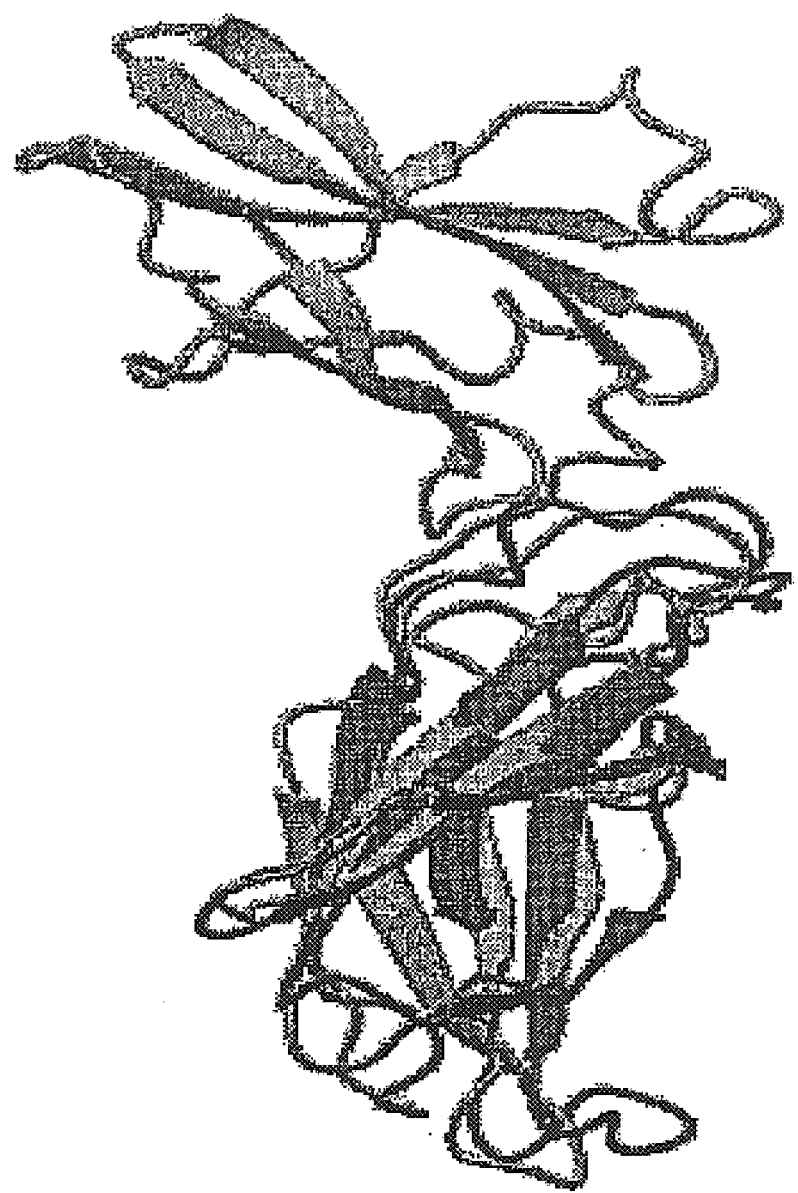
FIG. 3 illustrates a homology model for GCSFR, the granulocyte colony stimulating factor receptor (indicated in light grey) vs. the NMR structure of its fragment (indicated in dark grey).

In one aspect of this embodiment, modeling of the GCSF receptor sequence is performed onto the hGHR structure. GCSF receptor belongs to the same class of receptor family as hGHR. The resulting model structure is strikingly similar to the NMR structure of a GCSF receptor fragment containing WSXWS (SEQ ID NO: 30) motif (FIG. 3).

In another embodiment, the x-ray structure obtained for a natural ligand, a natural receptor or a natural receptor complexed with its natural ligand from one species is used to design the corresponding human analogs. In one aspect of this embodiment, protein design, such as PDA has been used successfully to design human GCSF analogs based on a structural model of the bovine GCSF x-ray structure.

Except for residues involved in ligand binding, most residues on the receptor do not interact directly with the ligand. However, most receptor residues are structurally important for scaffolding the fibronectin type III (Fn3) domain that presents the binding epitopes. Thus, in another embodiment, protein design, such as PDA is used to redesign amino acid residues to stabilize the Fn3 scaffold as well as the relative orientation between the D1 and D2 domains.

The computational processing results in a set of optimized analog proteins. These optimized analog protein sequences are generally significantly different from the wild-type naturally occurring cell surface receptor sequence from which the backbone was taken.

Structurally defined analog proteins, in particular the receptor analogs, designed by e.g. PDA, are experimentally tested and validated in in vivo and in in vitro assays, as described further below, for e.g., by examining binding affinity to natural ligands and to high affinity agonists and/or antagonists. In addition to cell-free biochemical affinity tests, quantitative comparison are made comparing kinetic and equilibrium binding constants for the natural ligand to the naturally occurring receptor and to the receptor analogs. The kinetic association rate ($K_{on}$) and dissociation rate ($K_{off}$), and the equilibrium binding constants ($K_d$) can be determined using surface plasmon resonance on a BIAcore instrument following the standard procedure in the literature (Pearce et al., Biochemistry 38:81–89 (1999); incorporated by reference). For most receptors described herein, the binding constant between a natural ligand and its corresponding naturally occurring receptor is well documented in the literature. Comparisons with the corresponding naturally occurring receptors are made in order to evaluate the sensitivity and specificity of the receptor analogs. In particular, binding affinity to natural ligands and agonists is expected to increase relative to the naturally occurring receptor, while antagonist affinity should decrease. Receptor analogs with higher affinity to antagonists relative to the non naturally occurring receptors may also be designed by e.g. PDA.

The analog proteins and AP nucleic acids of the invention can be made in a number of ways. As will be appreciated by those in the art, it is possible to synthesize proteins using standard techniques well known in the art. See for example Wilken et al., Curr. Opin. Biotechnol. 9:412–26 (1998), hereby expressly incorporated by reference.

Alternatively, and preferably, the proteins and nucleic acids of the invention are made using recombinant techniques. In a preferred embodiment, when combinations of variable positions are to be made, the nucleic acids encoding the analog proteins are made using a variety of combinatorial techniques. For example, "shuffling" techniques such as are outlined in U.S. Pat. Nos. 5,811,238; 5,605,721 and 5,830,721, and related patents, all of which are hereby expressly incorporated by reference.

In a preferred embodiment, multiple PCR reactions with pooled oligonucleotides is done. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of variable positions.

In a preferred embodiment, the different oligonucleotides are added in relative amounts corresponding to a probability distribution table; that is, different amino acids have different probabilistic chances of being at a particular position. Thus, for example, if out of 1000 sequences, a given amino acid position has valine 35% of the time, leucine 26% of the time, and isoleucine 31% of the time, the multiple PCR reactions will result in full length sequences with the desired combinations of variable amino acids in the desired proportions.

The total number of oligonucleotides needed is a function of the number of positions being mutated and the number of mutations being considered at these positions:
(number of oligos for constant positions)+$M_1+M_2+M_3+\ldots M_n$=(total number of oligos required)
where $M_n$ is the number of amino acids considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being varied, or for more than one position being varied. The multiple positions being varied must be dose in sequence to prevent the oligo length from being impractical. For multiple variable positions on an oligonucleotide, particular combinations of variable residues can be included or excluded in the library by including or excluding the oligonucleotide encoding that combination. The total number of oligonucleotides required increases when multiple variable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, error-prone PCR is done. See U.S. Pat. Nos. 5,605,793, 5,811,238, and 5,830,721, all of which are hereby incorporated by reference. This can be done on the optimal sequence or on top members of the analog protein set in this embodiment, the gene for the optimal analog protein sequence found in the computational screen can be synthesized. Error prone PCR is then performed on the optimal sequence gene in the presence of oligonucleotides that code for the variable residues at the variant positions (bias oligonucleotides). The addition of the oligonucleotides will create a bias favoring the incorporation of the variations in the secondary library. Alternatively, only oligonucleotides for certain variations may be used to bias the library.

In a preferred embodiment, gene shuffling with error prone PCR can be performed on the gene for the optimal sequence, in the presence of bias oligonucleotides, to create a DNA sequence library that reflects the proportion of the variations. The choice of the bias oligonucleotides can be done in a variety of ways; they can chosen on the basis of their frequency, i.e. oligonucleotides encoding high variation frequency positions can be used; alternatively, oligonucleotides containing the most variable positions can be used, such that the diversity is increased; if the analog protein set is ranked, some number of top scoring positions can be used to generate bias oligonucleotides; random positions may be chosen; a few top scoring and a few low scoring ones may be chosen; etc. What is important is to generate new sequences based on preferred variable positions and sequences. Similarly, a top set of analog proteins may be "shuffled" using traditional shuffling methods or overlapping oligonucleotide methods.

Using the nucleic acids of the present invention which encode an analog protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the analog protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein, a replacement of the naturally occurring secretory leader sequence is desired. In this embodiment, an unrelated secretory leader sequence is operably linked to an AP encoding nucleic acid leading to increased protein secretion. Thus, any secretory leader sequence resulting in enhanced secretion of the analog protein, when compared to the secretion of the naturally occurring protein and its secretory sequence, is desired. Suitable secretory leader sequences that lead to the secretion of a protein are know in the art.

In another preferred embodiment, a secretory leader sequence of a naturally occurring protein or a analog protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the STAT or CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the an.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, components of an expression vector, such as the genes encoding the receptor analog, the ligand analog, or libraries of candidate ligands reside on one vector. Alternatively, in another embodiment, particularly when e.g., multiple and/or different monomers of a receptor analog are expressed within the same cell (as described herein), the genes encoding these monomers, the ligand analogs, or libraries of candidate ligands may reside on more than one expression vector. As will be appreciated by those in the art, all combinations are possible and accordingly, as used herein, this combination of components, contained within one or more vectors, which may be retroviral or not, is referred to herein as a "vector composition".

The AP nucleic acids are introduced into the cells, either alone or in combination with an expression vector. By "Introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The AP nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The analog proteins of the present invention are produced by culturing a host cell transformed either with an expression vector containing nucleic acid encoding an analog protein or with the nucleic acid alone, under the appropriate conditions to induce or cause expression of the analog protein. The conditions appropriate for analog protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculovirus used in insect cell expression systems is a lytic virus, and thus harvest time selection can be crucial for product yield. Appropriate host cells include yeast, bacteria, *archaebacteria*, fungi, and insect and animal cells, including mammalian cells. Of particular interest are *Drosophila melangaster* cells, *Saccharmmyces cerevisiae* and other yeasts, *E. coli, Bacillus subutilis*, SF9 cells, C129 cells, 293 cells, *Neurospora*, BHK, CHO, COS, *Pichia Pastoris*, etc.

In a preferred embodiment, the analog proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 2530 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen can be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for de-differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the AP nucleic acid.

In a preferred embodiment, the analog proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the analog protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences.

Furthermore, a bacterial promoter can include naturally occurring promoters of nonbacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgamo (SD) sequence and includes an initiation codon and a sequence 3–9 nucleotides in length located 3–11 nucleotides upstream of the initiation codon.

The expression vector may also include a signal peptide sequence that provides for secretion of the analog protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to the PA nucleic acid, are preferred.

In a preferred embodiment, the analog proteins of the invention are expressed in bacteria and displayed on the bacterial surface. Suitable bacterial expression and display systems are known in the art (Stahl and Uhlen, Trends Biotechnol. 15:18592 (1997): Georgiou et al., Nat. Biotechnol. 15:29 34 (1997); Lu et al., Biotechnology 13:36672 (1995); Jung et al., Nat Biotechnol. 16:57680 (1998); all of which are expressly incorporated by reference).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, analog proteins are produced in insect cells. Expression vectors for the transformation of insect cells, and in particular, baculovirus-based expression vectors, are well known in the art.

In a preferred embodiment, analog proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the add phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, the analog proteins of the invention are expressed in yeast and displayed on the yeast surface. Suitable yeast expression and display systems are known in the art (Boder and Wittrup, Nat. Biotechnol. 15:553–7 (1997); Cho et al., J. Immunol. Methods 220:179–88 (1998); all of which are expressly incorporated by reference). Surface display in the ciliate *Tetrahymena thermophila* is described by Gaertig et al. Nat. Biotechnol. 17:462–465 (1999), expressly incorporated by reference.

In one embodiment, analog proteins are produced in viruses and are expressed on the surface of the viruses. Expression vectors for protein expression in viruses and for display, are well known in the art and commercially available (see review by Felici et al., Biotechnol. Annu. Rev. 1:149–83 (1995)).

Examples include, but are not limited to M13 (Lowman et al., (1991) Biochemistry 30:10832–10838 (1991); Matthews and Wells, (1993) Science 260:1113–1117; Stratagene); fd (Krebber et al., (1995) FEBS Lett. 377:227–231); T7 (Novagen, Inc.); T4 (Jiang et al., Infect. Immunol. 65:4770–7 (1997); lambda (Stolz et al., FEBS Lett. 440:213–7 (1998)); tomato bushy stunt virus (Joelson et al., J. Gen. Virol. 78:1213–7 (1997)); retroviruses (Buchholz et al., Nat. Biotechnol. 16:9514 (1998)). All of the above references are expressly incorporated by reference.

In addition, the analog proteins of the invention may be further fused to other proteins, if desired, for example to increase expression.

In one embodiment, the AP nucleic acids, proteins and antibodies of the invention may be labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the analog proteins may be covalently modified. One type of covalent modification includes reacting targeted amino acid residues of an analog protein with an organic derivatizing agent that is capable of reacting with selected side chains or the Nor O-terminal residues of an analog protein. Derivatization with bifunctional agents is useful, for instance, for crosslinking an analog protein to a water-insoluble support matrix or surface for use in the method for purifying anti analog protein antibodies or screening assays, as is more fully described below. Commonly used crosslinking agents include, e.g., 1,1-bis(diazoacetyl)$_2$-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the analog protein included within the scope of this invention comprises altering the native glycosylation pattern of the corresponding naturally occurring protein. "Altering the native glycosylation pattern" is intended for purposes herein to mean deleting one or more carbohydrate moieties found in the naturally occurring protein, and/or adding one or more glycosylation sites that are not present in the naturally occurring protein.

Addition of glycosylation sites to a analog protein may be accomplished by altering the amino acid sequence thereof. The alteration may be made, for example, by the addition of, or substitution by, one or more serine or threonine residues to the naturally occurring protein (for clinked glycosylation sites). The analog protein amino acid sequence may optionally be altered through changes at the DNA level, particularly by mutating the DNA encoding the analog protein at preselected bases such that codons are generated that will translate into the desired amino acids.

Another means of increasing the number of carbohydrate moieties on the analog protein is by chemical or enzymatic coupling of glycosides to the polypeptide. Such methods are described in the art, e.g., in WO 87/05330, published Sep. 11, 1987, and in Aplin and Wriston, CRC Crit. Rev. Biochem., pp. 259–306 (1981).

Removal of carbohydrate moieties present on the analog protein may be accomplished chemically or enzymatically or by mutational substitution of codons encoding for amino acid residues that serve as targets for glycosylation. Chemical deglycosylation techniques are known in the art and described, for instance, by Hakimuddin et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of an analog protein comprises linking the analog protein to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Analog proteins of the present invention may also be modified in a way to form chimeric molecules comprising an analog protein fused to another, heterologous polypeptide or amino acid sequence. In one embodiment, such a chimeric molecule comprises a fusion of an analog protein with a tag polypeptide which provides an epitope to which an anti-tag antibody can selectively bind. The epitope tag is generally placed at the amino-or carboxyl-terminus of the analog protein. The presence of such epitope-tagged forms of an analog protein can be detected using an antibody against the tag polypeptide. Also, provision of the epitope tag enables the analog protein to be readily purified by affinity purification using an anti-tag antibody or another type of affinity matrix that binds to the epitope tag. In an alternative embodiment, the chimeric molecule may comprise a fusion of an analog protein with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:21592165 (1988)]; the c-myc tag and the 8F9, 3C7, 6E10, G4, B7 and 9E10 antibodies thereto [Evan et al., Molecular and Cellular Biology, 5:3610–3616 (1985) 1; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:12041210 (1988)]: the KT3 epitope peptide [Martin et al., Science, 255:192–194(1992)]; tubulin epitope peptide [Skinner et al., J. Biol. Chem., 266:1516315166 (1991)]; and the T7 gene 10 protein peptide tag (Lutz-Freyermuth et al., Proc. Natl. Acad. Sci. USA, 87:6393–6397 (1990)].

In a preferred embodiment, the analog protein is purified or isolated after expression. Analog proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the analog protein may be purified using a standard anti-library antibody column. Ultrafiltration and diafiltration techniques, in conjunction with protein concentration, are also useful. For general guidance in suitable purification techniques, see Scopes, R., Protein Purification, Springer-Veriag, N.Y. (1982). The degree of purification necessary will vary depending on the use of the analog protein. In some instances no purification may be necessary. A preferred method for purification is outlined in the examples.

Once made, the analog proteins and nucleic acids of the invention find use in a number of applications.

In a preferred embodiment, the receptor analogs are used in methods designed for high throughput screening for ligand analogs and bioactive agents.

In a preferred embodiment, the receptor analogs are used in a method of screening for ligand analogs, comprising adding a candidate ligand to a receptor analog or to a naturally occurring receptor. By "candidate ligand" or grammatical equivalents thereof, herein is meant any molecule, e.g., protein, small organic molecule, polysaccharide, lipid, polynucleotide, etc., or mixtures thereof with the capability of binding to a receptor analog or to a naturally occurring receptor. Included within this definition are any molecules, as defined above, that have the capability to modulate the signaling activity of a receptor analog or of a naturally occurring receptor. "Modulating the signaling activity of a receptor analog or of a naturally occurring receptor" by a candidate ligand includes an increase (i.e., more efficient signaling of a receptor analog or of a naturally occurring receptor) or a decrease (i.e., less efficient signaling of a receptor analog or of a naturally occurring receptor), when compared to the signaling activity of a receptor analog or of a naturally occurring receptor in the absence of a candidate ligand. Assays used to determine signaling activity of naturally occurring cell surface receptors are also used to determine the signaling activity of the receptor analogs of the invention. These assays are known in the art and some are described further below.

A candidate ligand, once shown to bind to a receptor analog or to a naturally occurring receptor or modulates its activity is termed a "ligand analog." Of particular interest are candidate ligands that either have a low or no toxicity for human cells. Candidate ligands may be added as individual ligands, as combined samples of individual ligands or as more complex libraries as is discussed further below. Generally a plurality of assay mixtures is run in parallel with different candidate ligand concentrations to obtain a differential response to the various concentrations. Typically, one of these concentrations serves as a negative control, i.e., at zero concentration or below the level of detection.

Candidate ligands encompass numerous chemical classes, though typically they are organic molecules, preferably small organic compounds having a molecular weight of more than 100 and less than about 2,500 daltons. Candidate ligands comprise functional groups necessary for structural interaction with proteins, particularly hydrogen bonding, and typically include at least an amine, carbonyl, hydroxyl or carboxyl group, preferably at least two of the functional chemical groups. The candidate ligands often comprise cyclical carbon or heterocyclic structures and/or aromatic or polyaromatic structures substituted with one or more of the above functional groups. Candidate ligands are also found among biomolecules including peptides, saccharides, fatty acids, steroids, purines, pyrimidines and derivatives, structural analogs or combinations thereof. Particularly preferred are peptides. In fact, virtually any small organic molecule that is potentially capable of binding to a receptor analog or to a naturally occurring receptor of interest may find use in the present invention provided that it is sufficiently soluble and stable in aqueous solutions to be tested for its ability to bind to the receptor analog or to the naturally occurring receptor analog.

Candidate ligands are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate ligands are proteins.

In another preferred embodiment, the candidate ligands are naturally occurring proteins, fragments of naturally occurring proteins, ligand analogs, as described above, or fragments of ligand analogs. Thus, for example, cellular extracts containing proteins, or random or directed digests of proteinaceous cellular extracts, may be used. In this way libraries of prokaryotic and eukaryotic proteins may be made. Particularly preferred in this embodiment are libraries of bacterial, fungal, viral, and mammalian proteins, with the latter being preferred, and human proteins being especially preferred.

In a preferred embodiment, the candidate ligands are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each peptide consists of essentially random amino acids. Since generally these random peptides are chemically synthesized, they may incorporate any amino acid at any position. The synthetic process can be designed to generate randomized proteins to allow the formation of all or most of the possible combinations over the length of the sequence, thus forming a library of randomized candidate proteinaceous ligands.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or the like.

In one embodiment, a library of protein encoding nucleotide sequences may be obtained from genomic DNA, from cDNAs or from random nucleotides. Particularly preferred in this embodiment are libraries encoding bacterial, fungal, viral, and mammalian proteins and peptides, with the latter being preferred, and human encoding proteins and peptides being especially preferred. As described above and as known in the art the protein and peptide encoding nucleotide sequences may be inserted into any vector suitable for expression in mammalian cells, other eukaryotic cells, prokaryotic cells and viruses.

In a preferred embodiment, a library of candidate ligands is generated using protein design such as the PDA methodology, described herein. In this embodiment, a virtual library of candidate ligands is first generated and evaluated for its potential to generate candidate ligands capable of binding to a receptor analog of the invention. Following this analysis, an experimental random library is generated that is only randomized at the readily changeable, non-disruptive sequence positions of a naturally occurring protein. Thus, by limiting the number of randomized positions and the number of possibilities at these positions, the probability of finding sequences with useful properties does increase.

In another preferred embodiment, the candidate ligands are obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

Two types of assays are generally used for high throughput screening in drug discovery: (1) cell-free (i.e., biochemical assays or in vitro assays), which measure the binding affinity between a ligand and a receptor, and (2) cell-based assays, which measure the biological response triggered by the interaction between a ligand and a receptor displayed on the cell surface. Cell-free assays have several advantages over cell-based assays: (i) A far larger library may be screened allowing e.g., the use of highly diverse encoded small molecule libraries or peptide libraries, thereby greatly increasing the likelihood of a hit (ii) a greater sensitivity in comparison to cell-based assays allows lower affinity molecules to be identified. Cell-based assays (I) generally require reporter gene expression or downstream signals to be detected, (ii) are generally more time-consuming, and (iii) are generally more expensive than cell-free assays. However, the signaling activity of a receptor or receptor analog, usually the biological response upon binding of a cognate ligand, does involve cellular components and as such the biological activity of ligand analogs or bioactive agents identified in cell-free assays, is generally verified in cell-based assays. Thus, the present invention provides receptor analogs useful in methods of screening in cell-free assays and/or cell-based assays.

As outlined above, the novel receptor analogs of the present invention are useful for high throughput screening of ligand analogs and/or bioactive agents. The receptor analogs employed in the screening methods, detailed herein, are designed to maintain a stable, biologically active structure when used in cell-free assays or in in vitro assays.

In another preferred embodiment a library of candidate ligands is used in in vitro binding assays to detect binding of a candidate ligand to a receptor analog bound non-diffusably to an insoluble support having isolated sample receiving areas (e.g. a microtiter plate, an array, etc.). These assays are particularly useful for high throughput screening for ligand analogs. The insoluble support may be made of any composition to which the receptor analog can be bound, is readily separated from soluble material, and is otherwise compatible with the overall method of screening. The surface of such a support may be solid or porous and of any convenient shape. Examples of suitable insoluble supports include microliter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the receptor analog is not crucial so long as it is compatible with the reagents and overall methods of the invention, maintains the characteristics of the receptor analog and is non-difusable. The receptor analog may be either bound directly to the insoluble support (e.g. via cross-linking) or indirectly (e.g., via antibody, other protein or nucleic acid, etc.). Preferred methods of binding include the use of antibodies (which do not sterically block the interaction surface for the candidate ligand and preferably are directed against a tag polypeptide which may be incorporated into the surface receptor analog), direct binding to "sticky" or ionic supports, chemical crosslinking, etc. Following binding of the receptor analog, excess unbound material is removed by washing. The sample receiving areas may then be blocked through incubation with bovine serum albumin (BSA), casein or other innocuous protein.

The candidate ligand is added to the binding assay. Determination of the binding of the candidate ligand to the receptor analog may be done using a wide variety of assays, including labeled in vitro protein—protein binding assays, electrophoretic mobility shift assays (EMSA), immunoassays for protein binding, functional assays (phosphorylation assays, etc.) and the like. (e.g., see, Harlow and Lane, *Antibodies: A Laboratory Manual* (New York, Cold Spring Harbor Laboratory Press, 1988) and Ausubel et al., Short Protocols in Molecular Biology (John Wiley & Sons, Inc., 1995).

By "labeled" herein is meant that the compound (e.g., the candidate ligand which is tested for binding) is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the candidate ligand may be labeled at tyrosine positions using $^{125}$I, or at methionine positions using $^{35}$S, or with fluorophores. Alternatively, more than one component may be labeled with different labels using $^{125}$I or $^{35}$S for one protein, for example, and a fluorophor for a potential additional component.

In a preferred embodiment, the candidate ligand is labeled, and binding is determined directly. For example, this may be done by attaching all or a portion of receptor analog to a solid support, adding a labeled candidate ligand (for example a fluorescent label), washing off excess reagent, and determining whether the label is present on the solid support. Various blocking and washing steps may be utilized as is known in the art In another preferred embodiment, the candidate ligand and the receptor analog are combined first and after a certain incubation period, one protein, preferably the non-labeled protein (e.g. receptor analog) is bound either directly or indirectly to an insoluble support. The second protein, preferably labeled (e.g., the candidate ligand) which is bound to the receptor analog is visualized in accordance with the label incorporated.

Exemplified herein by the naturally occurring EPOR and/or EPOR analogs (as described above), but applicable to all naturally occurring receptors and receptor analogs of the invention, the naturally occurring EPOR and/or EPOR analogs are immobilized following standard procedures in the literature. Binding conditions may be further optimized for increased immobilization. Immobilization may be tested by determining the binding affinity of the natural ligand. The goal is to have an active and robust immobilized receptor analog for use in methods of screening for ligand analogs and bioactive agents (as described herein). Several methods, known to the skilled artisan, are used to immobilize the EPOR analog.

In one embodiment, the EPOR and/or EPOR analog is immobilized by attaching its free sulfhydryl group to Sulfolink agarose beads (Pierce Chemical Co), as described in the literature.

In another embodiment, the EPOR and/or EPOR analog or their disulfide-linked dimer are coated on Maxisorp microtiter plates (NUNC, Roskilde, Denmark), following published protocols.

In a preferred embodiment, the EPOR and/or EPOR analog containing a His-tag fusion peptide may be attached to a N-containing support, as described in the literature.

In another preferred embodiment, the EPOR and/or EPOR analog may be immobilized to a functional plate by cross-linking random lysines, as known in the art.

The binding assays described herein are exemplified by the natural occurring EPOR, EPOR analogs, natural occurring EPO, EPO analogs, and peptide mimics, however, as outlined above apply to other receptors and ligands, both naturally occurring and analogs thereof.

In one aspect of this embodiment, the equilibrium and kinetic constants between EPO or its mimics (e.g., EMP1) and immobilized receptor analogs using surface plasmon resonance (SPR) is measured.

Following literature procedures, the naturally occurring EPOR, EPOR analogs or their disulfide-linked homodimers are coupled to the sensor chip by random lysines to yield two different resonance units (RU), and the dissociation and association rates are determined by global fitting. The equilibrium constant is given by $K_d = K_{off}/K_{on}$.

In another embodiment, the equilibrium constant is determined using competition binding assay. Using the EPOR attached to sulfolink agarose, $^{125}I$ labeled EPO is used in competition assays with EPO and EPO mimetic peptides to measure the equilibrium constant between EPOR and ligand following standard procedures. Comparison of the equilibrium constant between the naturally occurring EPOR and EPO (or EPO mimetic peptides) with those from EPOR analogs provide a quantitative comparison on the EPOR analogs with EPO and its peptide mimetics.

Biophysical characterization is used to assess protein design and binding studies. Increased stability and oligomerization state both suggest a successful design. Also, receptor robustness is tested here. The following biochemical characterization is exemplified by the naturally occurring EPOR and/or EPOR analogs, but is applicable to all naturally occurring receptors and receptor analogs of the invention, In a preferred embodiment the stoichiometry of EPOR analogs in complex with EPO, EPO analogs, or EPO mimetics is determined. In one aspect of th is embodiment, size exclusion chromatography (SEC) is used to evaluate the receptor dimerization in the presence or absence of EPO, EPO analogs, or EPO mimetics, as shown in the literature. EPO, EPOR and disulfide-linked EPOR homodimer are used, together with protein standards, to calibrate the system. In another aspect of this embodiment, equilibrium sedimentation is used to confirm the result from SEC if necessary. EPOR analogs are expected to elute as dimers due to their stabilized complex conformation.

In another preferred embodiment, the binding constant between EPOR analogs and EPO, EPO analogs, or EPO mimetics is estimated using SEC at various ratios of EPOR analog vs. EPO, EPO analogs, or EPO mimetics, this results in useful information with respect to the bind ing affinity of EPOR analogs relative to each other.

In a preferred embodiment the stability of naturally occurring EPOR and EPOR analogs is monitored by circular dichroism (CD) and fluorescence upon thermal dim or chemical denaturation, as is known in the art.

In another embodiment, the conformational stability or mobility of naturally occurring EPOR and EPOR analogs is determined. As described in the literature, fluorescence can monitor the interface between two receptors by dye quenching and energy transfer.

In a preferred embodiment, the shelf life of EPOR analogs and EPO analogs is determined at various conditions. In particular at conditions used for screening. This can, e.g., be performed by incubating the proteins at high temperature and analyzing the protein left as a function of incubation time by analytical HPLC.

In a preferred embodiment, receptor analogs (i.e. structurally constrained receptors) are tested for their ability to screen phage displayed peptide libraries for agonists and antagonists. Standard phage library generation techniques are used to create libraries.

In a preferred embodiment, the present invention provides methods of screening for ligand analogs that are capable of binding to a receptor analog using a cell-based assay. Whenever available and applicable, a naturally occurring receptor and/or a naturally occurring ligand is/are used as a control within the assays outlined below. Briefly, a labeled candidate ligand analog is added to a cell comprising a receptor analog of the invention or a naturally occurring receptor and binding of the labeled candidate ligand analog is detected by virtue of the label as described above.

In a preferred embodiment, a plurality of cells is screened. By a "plurality of cells" herein is meant roughly from about $10^3$ cells to $10^8$ or $10^9$, with from $10^6$ to $10^8$ being preferred. This plurality of cells comprises a cellular library, wherein generally each cell within this cellular library contains a member of the molecular library, i.e. a different candidate ligand analog or a different ligand analog encoding nucleic add, although as will be appreciated by those in the art, some cells within the cellular library may not contain a member of the molecular library, and some may contain more than one. Methods such as retroviral infection, electroporation and others known in the art can be used to introduce the candidate analog protein into a plurality of cells; the distribution of candidate nucleic adds within the individual cell members of the cellular library may vary widely, depending on the method used.

As used in this specification and the appended claims, the singular forms "a", "an" and "the" include plural references unless the content clearly dictates otherwise. Likewise, plural forms, unless the content clearly dictates otherwise, include singular references. Thus, reference to "a monomer" includes mixtures of monomers, reference to a "receptor analog" includes mixtures of receptor analogs, and the like. Likewise, reference to "cells" Includes a cell, and the like.

In a preferred embodiment, the receptor analogs of the invention are used in cell based assays to screen for ligand analogs that have the ability to modulate the signaling of receptor analogs and or the signaling of naturally occurring cell surface receptors. Receptor signaling generally leads to an altered phenotype of the host cell or to a change in cell physiology.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAS, mRNAs, proteins, lipids, hormones, cytokines, or other molecules; changes in the equilibrium state (i.e. half-life) of one or more RNAs, mRNAs, proteins, lipids, hormones, cytokines, or other molecules; changes in the localization of one or more RNAs, mRNAs, proteins, lipids, hormones, cytokines, or other molecules; changes in the bioactivity or specific activity of one or more RNAs, mRNAs, proteins, lipids, hormones, cytokines, receptors, or other molecules; changes in the secretion of ions, cytokines, hormones, growth factors, proteins, or other molecules; alterations in cellular membrane potentials, polarization, integrity or transport; changes in infectivity, susceptibility, latency, adhesion, and uptake of viruses and bacterial pathogens; etc.

By "capable of altering the phenotype" or grammatical equivalents, herein is meant that a candidate ligand analog can change the phenotype of the cell in some detectable and/or measurable way.

The altered phenotype may be detected in a wide variety of ways, as is described more fully below and in PCT/US97/01019, and will generally depend and correspond to the phenotype that is being changed. Generally, the changed phenotype is detected using, for example: microscopic analysis of cell morphology; standard cell viability assays, including both increased cell death and increased cell in) viability, for example, cells that are now resistant to cell death via virus, bacteria, or bacterial or synthetic toxins; standard labeling assays such as fluorometric indicator assays for the presence or level of a particular cell or molecule. Including FACS or other dye staining techniques; biochemical detection of the expression of target compounds after killing the cells; monitoring changes in gene expression within a target cell, etc. In some cases, as is more fully described herein, the altered phenotype is detected in the cell in which the molecular library comprising the randomized nucleic acid or randomized proteins was introduced; in other embodiments, the altered phenotype is detected in a second cell which is responding to some molecular signal from the first cell.

In one aspect of this embodiment, the candidate ligand analogs, as part of a molecular library, generally are added to suitable host cells or are introduced into suitable host cells to screen for ligand analogs, capable of altering the phenotype of the host cell, harboring or expressing a receptor analog. If necessary, the cells are treated to conditions suitable for the expression of genes encoding the candidate analog proteins (for example, when inducible promoters are used), to produce the candidate expression products.

In another aspect of this embodiment, the methods of the present invention comprise introducing a molecular library of randomized candidate nucleic adds into a plurality of cells, generating a cellular library. Each of the nucleic acids comprises a different, generally randomized, nucleotide sequence, encoding a different ligand analog. The plurality of cells is then screened, as is more fully outlined below, for a cell exhibiting an altered phenotype. The altered phenotype is generally due to the presence of a ligand analog.

The present invention further provides methods of screening for ligand analogs that are capable of modulating the signaling activity of a receptor analog.

In a preferred embodiment, the method of screening for ligand analogs that are capable of modulating the signaling activity of a receptor analog comprises the steps of (1) providing a host cell comprising a vector composition, comprising a gene encoding a receptor analog. This vector composition may or may not comprise retroviral vectors, and may or may not be integrated into the genome of the host cell. (2) The host cell is subjected to conditions under which the gene encoding the receptor analog is expressed to produce a receptor analog. Optionally, it is determined (3) whether the receptor analog is displayed on the surface of the host cell, e.g., by using immunohistochemical and other methods as known in the art. (4) Optionally a natural ligand known to bind and activate a corresponding naturally occurring cell surface receptor is added. (5) Optionally the signaling activity of the receptor analog in response to the natural ligand is determined. (6) Candidate ligands that are capable of modulating the signaling activity of the receptor analog are added. Simultaneously, sequentially or at a later step (7) the modulation of the signaling activity of the receptor analog in response to the candidate ligand is determined by screening the cell for an altered phenotype or changed physiology e.g., by using cytokine, cell proliferation, cell differentiation assays, and other assays that are further described below. Preferably, (6) the candidate ligands are identified. Candidate ligands identified by this method are named ligand analogs.

In another preferred embodiment, the method of screening for ligand analogs that are capable of modulating the signaling activity of a receptor analog comprises the steps of (1) providing a host cell comprising a vector composition, comprising vector composition comprising a gene encoding a receptor analog and a gene encoding a natural ligand that is capable of binding to and activating the receptor analog. This vector composition may or may not comprise retroviral vectors, and may or may not be integrated into the genome of the host cell. (2) The host cell is subjected to conditions under which the genes encoding the receptor analog and the natural ligand are expressed to produce a receptor analog and a natural ligand. Optionally, ft is determined (3) whether the receptor analog is displayed on the surface of the host cell, e.g., by using immunohistochemical and other methods as known in the art. (4) Optionally the signaling activity of the receptor analog in response to the natural ligand is determined. (5) Candidate ligands that are capable of modulating the signaling activity of the receptor analog are added. Simultaneously, sequentially or at a later step (7) the modulation of the signaling activity of the receptor analog in response to the candidate ligand is determined by screening the cell for an altered phenotype or changed physiology e.g., by using cytokine, cell proliferation, cell differentiation assays, and other assays that are further described below.

Preferably, (6) the candidate ligands are identified. Candidate ligands identified by this method are named ligand analogs.

In a preferred embodiment a library of candidate ligands is added to a host cell comprising a receptor analog of the invention.

In another preferred embodiment a library of candidate ligands is added to a host cell displaying a receptor analog on its surface.

In another preferred embodiment a library of candidate ligands is added to a virus displaying a receptor analog on its surface.

As outlined above ligand analogs or bioactive agents (as further outlined below) of the present invention may modulate signaling activity of a receptor analog and as such they may exhibit cytokine, cell proliferation (either inducing or inhibiting), cell differentiation (either inducing or inhibiting), chemotactic or chemokinetic activity. The activity of the proteins of the invention, comprising receptor analogs, ligand analogs and bioactive agents may, among other means, be measured using a variety of assays.

In one embodiment, the natural ligands, known peptide agonists and known antagonists are used to measure the EC50 for proliferation and the level of JAK2 tyrosine kinase phosphorylation in cytokine receptor-responsive cell lines.

In another embodiment, binding affinities of fluorescently labeled natural ligands, known peptide agonists and known antagonists to receptor analogs and naturally occurring cell surface receptors are assayed by competition assays.

In a preferred embodiment, assays for proliferation and differentiation of hematopoietic and lymphopoietic cells are provided that include, but are not limited to those described in: Current Protocols in Immunology (Ed by J. E. Coligan et al. Vol 1; Greene Publishing Associates and Wiley-Interscience; John Wiley and Sons, Toronto (1994)); derives et al., J. Exp. Med. 173:1205–1211 (1891); Moreau et al., Nature 336:690–692 (1988); Greenberger et al., Proc. Natl. Acad. Sc. U.S.A. 83:1857–1861 (1986); incorporated as references in their entirety.

In another embodiment, assays for T-cell or thymocyte proliferation are provided that include, but are not limited to those described in: *Current Protocols in Immunology*, supra; Takai et al., J. Immunol. 137:3494–3500 (1986); Bertagnolli et al., J. Immunol. 145:1706–1712 (1990); Bertagnoil et al., Cellular Immunology 133:327–341 (1991); Bertagnolli et al., J. Immunol. 149:3778–3783 (1992); Bowman et al., J. Immunol. 152:17561761 (1994); incorporated as references in their entirety.

In another embodiment, assays for cytokine production and/or proliferation of spleen cells, lymph node cells or thymocytes are provided that include, but are not limited to those described in: *Current Protocols in Immunology*, supra.

In one embodiment, assays for T-cell clone responses to antigens are provided that include, but are not limited to those described in: *Current Protocols in Immunology*, supra; Weinberger et al., Proc Natl. Acad. Sd. U.S.A. 77:6091–6095 (1980); Weinberger et al., Eur. J. Immunol. 11:405–411 (1981); Takai et al., J. Immunol. 137:3494–3500 (1986); Takai et al., J. Immunol. 140:508–512 (1988); incorporated as references in their entirety.

In a preferred embodiment assays for thymocyte or splenocyte cytotoxicity are provided that include, but are not limited to those described in: *Current Protocols in Immunology*, supra; Hermann et al., Proc. Natl. Acad. Sci. U.S.A. 78:24882492 (1981); Herman et al., J. Immunol. 128:19681974 (1982); Handa et al., J. Immunol. 135:1564–1572 (1985); Takai et al., J. Immunol. 137:3494–3500 (1986); Takai et al., J. Immunol. 140:508512 (1988); Bowman et al., J. Virology 61:1992–1998; Bertagnolli et al., Cellular Immunology 133:327–341 (1991); Brown et al., J. Immunol. 153:3079–3092 (1994); incorporated as references in their entirety.

In one embodiment assays for T-cll-dependent immunoglobulin responses and isotope switching are provided that include, but are not limited to those described in: Mallszewski, J. Immunol. 144:3028–3033 (1990); incorporated as reference in its entirety.

In another embodiment assays for B cell function are provided that include, but are not limited to those described in: *Current Protocols in Immunology*, supra;

In another embodiment, mixed lymphocyte reaction (MLR) assays are provided that include, but are not limited to those described in: Current Protocols in Immunology, supra; Takai et al., J. Immunol. 137:3494–3500 (1986); Takai et al., J. Immunol. 140:508–512 (1988); Bertagnolli et al., J. Immunol. 149:3778–3783 (1992); incorporated as reference in their entirety.

In a preferred embodiment, dendritic cell-dependent assays are provided that include, but are not limited to those described in: Guery et al., J. Immunol. 134:536–544 (1995); Inaba et al., J. Exp. Med. 173:549–559 (1991); Macatonia et al., J. Immunol. 154:5071–5079 (1995); Porgador et al., J. Exp. Med. 182:255–260 (1995); Nair et al. J. Virology 67:4062–4069 (1993); Huang et al., Science 264:961–965 (1994); Macatonia et al., J. Exp. Med. 169:1255–1264 (1989); Bhardwaj et al., J. Clinic. Invest. 94:797–807 (1994); Inaba et al., J. Exp. Med. 172:631–640 (1990); incorporated as reference in its entirety.

In another embodiment assays for lymphocyte survival/apoptosis are provided that include, but are not limited to those described in: Darzynkiewicz et al., Cytometry 13:795–808 (1992); Gorczyca et al., Leukemia 7:659–670 (1993): Gorczyca et al., Cancer Research 53:1945–1951 (1993); Ktoh et al., Cell 66:233–243 (1991); Zacharchuk, J. Immunol. 145:4037–4045 (1990); Zamai et al., Cytometry 14: 891–897 (1993); Gorczyca et al., Intl. J. Oncology 1:639–648 (1992); incorporated as references in their entirety.

In a preferred embodiment, assays for proteins that influence early steps of T-cell commitment and development are provided that include, but are not limited to those described in: Antica et al., Blood 84:111–117 (1994); Fine et al., Cell. Immunol. 155:111–122 (1994); Galy et al., Blood 85:2770–2778 (1995); Toki et al., Proc. Nat. Acad. Sci. U.S.A. 88: 7548–7551 (1991); incorporated as references in their entirety.

In another preferred embodiment, assays for proliferation and differentiation of various hematopoietic cells are provided (cited above).

In one embodiment, assays for embryonic stem cell differentiation are provided that include, but are not limited to those described in: Johansson et al., Cell. Biol. 15:141–151 (1995); Keller et al., Mol. Cell. Biol. 13:473–486 (1993); McClanahan et al., Blood 81:2903–2915 (1993); incorporated as references in their entirety.

In a further embodiment assays for stem cell survival and differentiation are provided that include, but are not limited to those described in: *Culture of Hematopoietic Cells* (R. I. Freshney et al., eds. Wiley-Liss, Inc. New York 1994); Hirayama et al., Proc. Natl. Acad. Sci. U.S.A. 89:5907–5911 (1992);

incorporated as references in their entirety.

In a preferred embodiment, assays for chemotactic activity are provided that include, but are not limited to those described in: Current Protocols in Immunology, supra; Taub et al., J. Clin. Invest. 95:1370–1376 (1995); Lind et al., APIMIS 103:140–146 (1995); Muller et al., Eur. J. Immunol. 25:1744–1748; Gruber et al., J. Immunol. 152:5860–5867 (1994); Johnston et al., J. Immunol. 153:1762–1768 (1994); incorporated as reference in their entirety.

In another preferred embodiment, assays for hemostatic and thrombolytic activity are provided that include, but are not limited to those described in: Linet et al., J. Clin. Pharmacol. 26:131–140 (1986); Burdick et al., Thrombosis Res. 45:413–419 (1987); Humphrey et al., Fibrinolysis 5:71–79 (1991); Schaub, Prostaglandins 35:467–474 (1988); incorporated as references in their entirety.

In another embodiment, assays for receptor-ligand activity are included and include, but are not limited to those described in: *Current Protocols in Immunology*, supra; Takai et al., Proc. Natl. Acad. Sci.

U.S.A 84:6864–6868 (1987); Blerer et al., J. Exp. Med. 168:1145–1156 (1988); Rosenstein et al., J. Exp. Med. 169:149–160 (1989); Stoltenberg et al., J. Immunol. Methods 175:59–68 (1994); Sitt et al., Cell 80:661–670 (1995); incorporated as reference in their entirety.

Generally, the biological activity of a cytokine is determined by cytokine receptor-mediated signal transduction events. Accordingly, the biological activity of a receptor analog can be determined by measuring the EC50 from cell proliferation and the level of tyrosine phosphorylation following standard procedures. Assays for determining biological activity are exemplified for the naturally occurring EPOR and/or EPOR analogs, but are applicable to all naturally occurring receptors and receptor analogs of the invention.

In a preferred embodiment, the EC50 is determined using a cell proliferation assay. In one aspect of this embodiment, FD-P1 cells are transfected with the full-length human EPOR, (which includes either a naturally occurring EPOR or a designed EPOR analog or comprises either a naturally occurring ECD or a designed ECD). EPO, EPO analogs and EMP are used to determine the EC50 by incubating them with the transfected cell following standard procedures.

In another preferred embodiment, the level of tyrosine phosphorylation is determined. In one aspect of this embodiment, FDP1 cells are transfected with the full-length human EPOR, (which includes either a naturally occurring EPOR or a PDA designed EPOR analog or comprises either a naturally occurring ECD or a PDA designed ECD). Following published procedures, these cells are stimulated by EPO, EPO analogs and EMP, and then processed and isolated by immunoprecipitation and electrophoresis. The phosphorylation level may be measured by immunoblotting antibodies.

Yeast and mammalian protein—protein interaction cloning systems (termed two-hybrid interaction screening systems) are described in the art (Fields et al., Nature 340:245 (1989); Vasavada et al., Proc. Natl. Acad. Sci. U.S.A. 88:10686 (1991); Fearon et al., Proc. Natl. Acad. Sc. U.S.A. 89:7958(1992); Dang et al., Mol. Cell. Biol. 11:954 (1991); Chien et al., Proc. Natl. Acad. Sc. U.S.A. 88:9578 (1991); Luo et al., Biotechniques 22:350–352 (1997); and U.S. Pat. Nos. 5,283,173; 5,667,973; 5,468,614; 5,525,490; and 5,637,463). The basic system requires a protein—protein interaction in order to turn on transcription of a reporter gene.

In a preferred embodiment, the receptor analogs of the invention are used in cell free assays to screen for ligand analogs that have the ability to modulate the signaling of receptor analogs and or the signaling of naturally occurring cell surface receptors.

In another preferred embodiment, the invention provides a three hybrid interaction system for the detection of ligand-receptor interaction in vivo. Briefly, the sequence of a receptor analog is fused to a DNA-binding domain, including, but not limited to those derived from Gal4 and LexA, to generate a DNA-binding-analog receptor fusion protein ("Fusion protein I"). Another receptor analog sequence is fused to a transcription activation domain including, but not limited to those derived from VP16 and Gal4 to generate a transcription-activation-domain-receptor analog fusion protein ("Fusion protein II). A reporter gene construct comprising a detectable marker and the genes encoding fusion proteins I and II are introduced into a eukaryotic cell (e.g., yeast or any mammalian cell) by methods known in the art. Detectable markers include, but are not limited to luciferase, GFP, etc. Fusion protein I has the capability to bind to a DNA binding site in the proximity of the transcriptional start site for the gene encoding the detectable marker. By adding a candidate ligand capable of binding to the analog receptor, and due to the binding of the candidate ligand to both receptor analogs, i.e. to those receptor analogs comprised by fusion proteins I and II, fusion protein II is recruited to fusion protein I that is bound to the promoter region of the detectable marker gene. As a consequence thereof, the transcription activation domain is brought into the vicinity of the transcriptional machinery and stimulates transcription of the detectable marker gene. The expression of the detectable marker is detected using various methods known in the art and depends on the detectable marker used.

In another aspect of this embodiment, a candidate bioactive agent is added and bioactive agents are identified that in the above described three-hybrid system, lead to an increase or decrease of reporter gene activity. Thereby, bioactive agents having the capability of stabilizing and/or destabilizing the ligand-receptor interaction are identified.

In a preferred embodiment, the invention provides methods for screening for bioactive agents that are capable of modulating the interaction between the receptor analog and the ligand analog.

In a preferred embodiment, the invention provides methods for screening for bioactive agents that are capable of modulating the interaction between the receptor analog and the ligand analog. "Modulating the interaction between the receptor analog and the ligand analog" includes an increase (i.e., tighter affinity between the receptor analog and the ligand analog), a decrease (i.e., lower affinity between the receptor analog and the ligand analog), or a change in the type or kind of this interaction. Both in vivo and in vitro systems (ceel free systems) are used in this invention to identify bioactive agents that are capable of modulating the interaction between the receptor analog and the ligand analog.

By "bioactive agent" or grammatical equivalents thereof herein is meant any molecule, e.g., protein, small organic molecule, polysaccharide, lipid, polynucleotide, etc., or mixtures thereof with the capability of modulate the interaction between the receptor analog and the ligand analog. Various classes and libraries of proteins, small organic molecules, polysaccharides, lipids, polynucleotides, etc. are described above and also apply with respect to bioactive agents. Further included within this definition are molecules, as defined above, with the capability of modulating the signaling activity of the receptor analog.

Addition of the candidate bioactive agent is performed under conditions which allow the modulation of the interaction between the receptor analog and the ligand analog or the modulation of the signaling activity of the receptor analog to occur. As will be appreciated by those in the art, those conditions will depend upon the nature of the interaction, the nature of the candidate bioactive agent, and are go determined routinely and empirically, as will the concentration of the candidate bioactive agents to be employed. Thus, in this embodiment, the candidate bioactive agent possesses a size or structure which allows binding to either receptor analog or the ligand analog (although this may not be necessary), and modulate the interaction between them. This modulation preferably results in a measurable change of the signaling activity of the receptor analog.

Accordingly, in one embodiment, the method of screening for bioactive agents that are capable of modulating the interaction between a receptor analog and a ligand analog comprises the steps of (1) providing a host cell comprising a vector composition, comprising a gene encoding a receptor analog and a gene encoding a ligand analog. This vector composition may or may not comprise retroviral vectors, and may or may not be integrated into the genome of the host cell. (2) The host cell is subjected to conditions under which the genes encoding the receptor analog and the ligand analog are expressed to produce a receptor analog and a ligand analog. Optionally, it is determined (3) whether the receptor analog is displayed on the surface of the host cell, e.g., by using immunohistochemical and other methods as known in the art. (4) Optionally it is determined whether the ligand analog is bound to the receptor analog. (5) Candidate bioactive agents that are capable of modulating the interaction between the receptor analog and the ligand analog are added. Simultaneously, sequentially or at a later step (6) the interaction between the ligand analog and the receptor analog is determined, e.g., by using cytokine, cell proliferation, cell differentiation assays, and other assays that are further described below. (7) The interaction between the ligand analog and the receptor analog in the presence of a bioactive agent is compared to the interaction between the ligand analog and the receptor analog in the absence of a bioactive agent. Preferably, (8) the bioactive agents are identified. Bioactive agents identified by the subject methods may find use as new small molecule drug leads, inhibitors, activators, diagnostic reagents, and the like.

In another preferred embodiment, the method of screening for bioactive agents that are capable of modulating the signaling activity of a receptor analog comprises the steps of (1) providing a host cell comprising a vector composition, comprising a gene encoding a receptor analog and a gene encoding a ligand analog. This vector composition may or may not comprise retroviral vectors, and may or may not be integrated into the genome of the host cell. (2) The host cell is subjected to conditions under which the genes encoding the receptor analog and the ligand analog are expressed to produce a receptor analog and a ligand analog. Optionally, it is determined (3) whether the receptor analog is displayed on the surface of the host cell, e.g., by using immunohistochemical and other methods as known in the art (4) Optionally it is determined whether the ligand analog is bound to the receptor analog. (5) Optionally the signaling activity of the receptor analog in response to the ligand analog is determined. (6) Candidate bioactive agents that are capable of modulating the signaling activity of the receptor analog are added. Simultaneously, sequentially or at a later step (7) the modulation of signaling activity of the receptor analog is determined, e.g., by using cytokine, cell proliferation, cell differentiation assays, and other assays that are further described below. (8) The signaling activity of the receptor analog in the presence of a bioactive agent is compared to the signaling activity of the receptor analog in the absence of a bioactive agent. Preferably, (9) the bioactive agents are identified. Bioactive agents identified by the subject methods may find use as new small molecule drug leads, inhibitors, activators, diagnostic reagents, and the like.

In another preferred embodiment of the above invention. Instead of providing a gene encoding a ligand analog, the method comprises the step of providing a gene encoding a natural ligand.

In another preferred embodiment of the above invention, instead of providing a gene encoding a ligand analog, the method comprises the step of providing the ligand analog as a recombinant protein to the host cell comprising a receptor analog.

In another preferred embodiment of the above invention, instead of providing a gene encoding a ligand analog, the method comprises the step of providing a natural ligand as a recombinant protein to the host cell comprising a receptor analog.

In a preferred embodiment, it is desired to screen for bioactive agents that are antagonists, i.e., the libraries of bioactive agents is used to identify bioactive agents that (i) decrease the interaction between the receptor analog and the analog ligand or natural ligand or (ii) decrease the signaling activity of the receptor analog.

In a preferred embodiment, it is desired to screen for bioactive agents that are agonists, i.e., the libraries of bioactive agents is used to identify bioactive agents that (i) increase the interaction between the receptor analog and the analog ligand or natural ligand or (ii) increase the signaling activity of the receptor analog.

In a preferred embodiment, the candidate bioactive agent or the candidate ligand is a protein which is encoded by a cDNA, cDNA fragment or genomic DNA fragment (for example, as part of a cDNA or genomic library) and is readily identified by rescuing the nucleic acid encoding the candidate bioactive agent. The nucleic acid sequence is determined. As known in the art, the obtained information may be used to isolate a full-length cDNA encoding the full-length candidate bioactive agent and to express the candidate bioactive agent as a recombinant protein. Preferably, the full-length recombinant candidate bioactive agent (either in form of a full-length cDNA or as a full-length protein) may be purified, labeled and used in in vivo and in in vitro binding assays (as outlined herein) to confirm e.g., its modulation of the signaling activity of a receptor analog.

In a preferred embodiment, the modulation of the signaling activity of a surface receptor analog by a candidate bioactive agent is optimized. The identified candidate bioactive agent is either chemically modified or the nucleic acid encoding the candidate bioactive agent is subjected to in vitro mutagenesis or to the PDA methodology, as described herein. These modifications result in the synthesis of candidate bioactive agent variants. Preferably, these variants are purified, labeled and used in in vivo and in in vitro binding assays (as outlined herein) to test their modulation of the signaling activity of receptor analog. These variants lead either to more potent, more tolerable or less toxic small molecule drug leads, inhibitors, activators, diagnostic reagents, and the like.

In a preferred embodiment, the efficacy of the candidate bioactive agent variant (i.e., its characteristics, its modulation of the signaling activity of the receptor analog, its binding to the receptor analog, etc.) is compared to the efficacy of the originally isolated candidate bioactive variant using in vitro binding assays and in vivo assays (as outlined herein). In this embodiment, the in vitro binding assays comprise at least four components: a receptor analog, a ligand analog (or a natural ligand), an originally identified candidate bioactive agent and a candidate bioactive agent variant.

In a preferred embodiment, the invention provides in vitro (i.e. cell free) methods for screening for bioactive agents that are capable of modulating the interaction between a receptor analog and a ligand analog.

In one embodiment, a receptor analog is bound to an insoluble support and a ligand analog (or natural ligand), which may be labeled. Is added and allowed to bind to the receptor analog. Incubations are performed at any temperature which facilitates optimal binding, typically between 4° C. and 40° C. Incubation periods are selected for optimum binding, but are also optimized to facilitate rapid high through put screening. Typically between 0.1 and 3 hour is sufficient. Excess of labeled ligand analogs (or natural ligands) is generally removed or washed away. The original candidate bioactive agent or a variant thereof is then added, and the presence or absence of the labeled ligand analog (or natural ligand) in the wash solution or supernatant is followed, to indicate a possible displacement by the candidate bioactive agent or its variant.

In this embodiment, displacement of the ligand analog (or natural ligand) is an indication that the candidate bioactive agent or a variant thereof is modulating the interaction between the receptor analog and the ligand analog (or natural ligand) and thus functions as antagonist. A displacement of more ligand analog (or natural ligand) by the candidate bioactive agent variant (i.e., when compared to the original candidate bioactive agent) indicates that the variant is a stronger antagonist which may be developed as a more potent small molecule drug lead. Inhibitor, activator, diagnostic reagent, or the like. Alternatively, a displacement of less ligand analog (or natural ligand) by the candidate bioactive agent variant (i.e., when compared to the original candidate bioactive agent) which indicates that the variant is a weaker antagonist can lead to the development of a more tolerable or less toxic small molecule drug lead, inhibitor, activator, diagnostic reagent, or the like.

In another embodiment, the original candidate bioactive agent or a variant thereof. Is added first to the receptor analog, which is bound to an insoluble support with incubation and washing, followed by the addition of the ligand analog (or natural ligand), which may be labeled, with incubation and washing. Absence of binding of the ligand analog (or natural ligand) or reduced binding thereof when compared to a control sample may indicate that the original bioactive agent is bound to the receptor analog with a high affinity and may mask the interaction surface for the ligand analog (or natural ligand). Alternatively, the original candidate bioactive agent may have changed the tertiary structure of the receptor analog and thereby rendered the receptor analog unable to functionally interact with the ligand analog (or natural ligand). More or less binding of the ligand analog (or natural ligand), when used in combination with the candidate bioactive agent variant (and when compared to the original candidate bioactive agent) indicates a weaker or stronger binding of the variant to the receptor analog. The ramifications drawn, are similar to those outlined above.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

The practice of the present invention will employ, unless otherwise indicated, conventional methods of chemistry, biochemistry, microbiology, molecular biology, cell biology, recombinant DNA techniques and computational analyses within the skill of the art. Such techniques are explained fully in the literature. All publications, patents and patent applications cited herein, whether supra or infra, are hereby incorporated by reference in their entirety.

EXAMPLE 1

Designing the EPOR Sequences Using PDA with Multiple Strategies and Structure Complexes Following the steps outlined above for designing receptor analogs using PDA, the following sequences using three structures of EPOR in 1ebp, 1eer and 1 blw (also called 1cn4) were designed, resulting in EPOR analogs (see FIG. 8).

A). First PDA Design: D1 and D2 domain
  1. PDA design of EPO receptors based on (EPOR+ EMP1)$_2$ dimer complex 1ebp, (EPOR)$_2$EPO complex 1eer, and 1blw.
  2. The core was divided into two subdomains: D1 and D2
  3. Sequences with better than wild type energy arechosen: two for D1 and only one for D2 and a combination of D1 and D2 using backbone independent rotamer libraries and one for D1 using backbone dependent rotamer library for 1ebp alone.

B). Second PDA Design:
  1. elbow_PDA design based on (EPOR+EMP1)$_2$ dimer complex 1 ebp, (EPOR)$_2$EPO complex 1eer, and 1blw.
  2. PDA design of EPOR elbow involving the buried residues between the interfaces of domain D1, domain D2, the N-terminal helix H and the WSXWS-box (SEQ ID NO: 30).
  3. Both the EPOR dimer and its monomers (amino acid residues 1–211) and (amino acid residues 222422) were designed and listed (see FIG. 8).

EXAMPLE 2

Fusion of Coiled Coil to EPOR Analogs

The designed EPOR analog is linked by a GGGGS (SEQ ID NO:35) linker sequence to a PDA designed coiled-coil sequence (RMEKLEQKVKELLRKNERLEEEVERLKQLVGER (SEQ ID NO:31), based on the GCN4 structure. For example: 1 ebpjdl2 GCN4 (SEQ ID NO: 37; see also Example 3) is composed of 1ebp_d12 (SEQ ID NO:6) (1ebp_d1 (SEQ ID NO:4) add 1ebp_d2 (SEQ ID NO:5) mutants together), plus GGGGS (SEQ ID NO:35), plus designed GCN4 sequence.

EXAMPLE 3

Cloning, Expression, Refolding, Purification and Characterization of EPOR Analogs Human wild type EPOR(amino acid positions 1–225) (called EPOR), its fusion construct linked by a GGGGS (SEQ ID NO: 35) linker sequence to a coiled-coil (called EPORGCN4) and a mutant linked by GGGGS (SEQ ID NO: 36) inker sequence to a coiled-coil (called 1ebp_d 12_GCN4) were cloned using standard techniques. The DNA sequences were synthesized using a series of overlap ping oligonucleotides and amplified by the polymerase chain reaction (PCR), cloned into the expression vector PET21a, and transfected into E coli. Some proteins were expressed in yeast using known methods in the art. Using standard techniques, the proteins were refolded from inclusion bodies and purified at the expected molecular weight using size-exclusion chromatography calibrated by standard proteins. These purified proteins were further purified using C4 reverse phase column chromatography to obtain the mass spectra of these proteins at the expected molecular weight. The proteins show cooperative thermal melting curves as monitored by circular dichroism (CD) (data not shown). A western blot analysis of all three proteins, EPOR and EPOR analogs with the EPOR antibody confirmed the expression, the size of the respective proteins and the crossreactivity with EPOR antibodies (data not shown).

We claim:

1. An erythropoietin receptor (EPOR) analog protein comprising SEQ ID NO: 37.

2. The EPOR analog protein according to claim 1 further comprising a linker.

3. The EPOR analog protein according to claim 2 further comprising a dimerization motif.

4. The EPOR analog protein according to claim 2 in which the linker is a peptide linker selected from the group consisting of (GS)$_n$, (GSGGS)$_n$ (SEQ ID NO: 34), (GGGGS)$_n$ (SEQ ID NO: 35), and (GGGS)$_n$ (SEQ ID NO: 36).

5. The EPOR analog protein according to claim 3 in which the dimerization motif is a coiled coil motif selected from the group consisting of RMEKLEQKVKELLRKNERLEEEVER LKQLVGER (SEQ ID NO: 31), AALESEVSALESEVASLESEVAAL (SEQ ID NO: 32), and LAAVKSKLSAVKSKLASVKSKLAA (SEQ ID NO: 33).

* * * * *